US011713441B2

(12) United States Patent
Chang

(10) Patent No.: US 11,713,441 B2
(45) Date of Patent: Aug. 1, 2023

(54) CELL CULTURE SUBSTRATES, METHODS AND USES THEREOF

(71) Applicant: Academia Sinica, Taipei (TW)

(72) Inventor: Ying-Chih Chang, Atherton, CA (US)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 17/958,234

(22) Filed: Sep. 30, 2022

(65) Prior Publication Data
US 2023/0091341 A1 Mar. 23, 2023

Related U.S. Application Data

(63) Continuation-in-part of application No. 17/566,179, filed on Dec. 30, 2021, now Pat. No. 11,492,598.

(60) Provisional application No. 63/252,268, filed on Oct. 5, 2021, provisional application No. 63/132,934, filed on Dec. 31, 2020.

(51) Int. Cl.
G01N 33/50 (2006.01)
C12N 5/09 (2010.01)
C12M 1/00 (2006.01)

(52) U.S. Cl.
CPC .......... *C12M 23/20* (2013.01); *C12N 5/0693* (2013.01); *G01N 33/5011* (2013.01); *G01N 33/5088* (2013.01); *C12N 2502/1164* (2013.01); *C12N 2513/00* (2013.01); *C12N 2533/32* (2013.01); *C12N 2533/40* (2013.01); *C12N 2533/50* (2013.01)

(58) Field of Classification Search
CPC .......... C12N 5/0693; C12N 2502/1164; C12N 2513/00; C12N 2533/32; C12N 2533/40; C12N 2533/50; G01N 33/5011; G01N 33/5088
See application file for complete search history.

(56) References Cited

U.S. PATENT DOCUMENTS

| 2011/0151564 A1 | 6/2011 | Menu et al. |
| 2013/0210140 A1 | 8/2013 | Burns et al. |
| 2014/0093962 A1 | 4/2014 | Ingram et al. |
| 2015/0299663 A1 | 10/2015 | Pachmann et al. |
| 2017/0166884 A1 | 6/2017 | Peterson et al. |
| 2019/0049432 A1 | 2/2019 | Kitano et al. |
| 2020/0095526 A1 | 3/2020 | Rothbauer et al. |
| 2022/0204944 A1 | 6/2022 | Chang |

FOREIGN PATENT DOCUMENTS

| EP | 3 421 588 A1 | 1/2019 |
| JP | 2006-246883 A | 9/2006 |
| KR | 10-2017-0060194 A | 6/2017 |
| WO | WO-2015/152612 A1 | 10/2015 |

OTHER PUBLICATIONS

Oshikata et al., Enhancement of drug efflux activity via MDR1 protein by spheroid culture of human hepatic cancer cells. Journal of Bioscience and Bioengineering, vol. 111, No. 5 (May 2011) pp. 590-593 (Year: 2011).*
Richert et al., PH dependent growth of poly(L-lysine)/poly(L-glutamic) acid multilayer films and their cell adhesion properties. vol. 570, No. 1-2 (Oct. 10, 2004) pp. 13-29 (Year: 2004).*
Dhiman et al., On-chip anticancer drug screening- recent progress in microfluidic platforms to address challenges in chemotherapy. Biosensors and Bioelectronics, vol. 137 (Jul. 15, 2019) pp. 236-254 (Year: 2019).*
Ishiguro et al., Establishment and characterization of an in vitro model of ovarian cancer stem-like cells with an enhanced proliferative capacity. Cancer Research, vol. 76, No. 1 (2016) pp. 150-160 (Year: 2016).*
Tu et al., Surface modification of poly(dimethylsiloxane) and its applications in microfluidics-based biological analysis. Rev Anal Chem, 31(3-4) (2012) pp. 177-192 (Year: 2012).*
Aref et al., 3D microfluidic ex vivo culture of organotypic tumor spheroids to model immune checkpoint blockade. Royal Society of Chemistry, vol. 18 (2019) pp. 3129-3143 (Year: 2019).*
Carver et al., Multicellular tumor spheroids as a model for assessing delivery of oligonucleotides in three dimensions. Molecular Therapy Nucleic Acids, vol. 3 (Jan. 2014) e153 (Year: 2014).*
Dillard et al. A spheroid killing assay by CAR T cells. JoVE Cancer Research, (Dec. 12, 2018) DOI:10.3791/58785 (Year: 2018).*
Arias, Carlos, J., et al., "Quasi-Spherical Cell Clusters Induced by a Polyelectrolyte Multilayer," 2015, Langmuir, 31, 23, 6436-6446.
Chen, et al., "Drug cytotoxicity and signaling pathway analysis with three-dimensional tumor spheroids in a microwell-based microfluidic chip for drug screening," Analytica Chimica Acta, 2015; 898:85-92.
Chen, et al., "High-throughput single-cell derived sphere formation for cancer stem-like cell identification and analysis," Scientific Reports, Jun. 13, 2016; 6:27301.
Detzel, Ph.D., Christopher, J., et al., "Polyelectrolyte Multilayers in Tissue Engineering," Tissue Engineering: Part B, vol. 17, No. 2, 2011, DOI:10.1089/ten.teb.2010.0548, pp. 101-113.
Dou, Xiaoqiu, et al., Three-Dimensional Microstructured Poly(vinyl alcohol) Hydrogel Platform for the Controlled Formation of Multicellular Cell Spheroids, 2018, Biomacromolecules, 19(1):158-166.
Facca, S., et al., "Active multilayered capsules for in vivo bone formation," 2010, PNAS, 107(8):3406-3411.
Final Office Action on U.S. Appl. No. 17/566,166 dated Aug. 19, 2022.
International Search Report dated Apr. 29, 2022 issued in International Application No. PCT/US2021/065694, 4 pages.
International Search Report dated May 2, 2022 issued in International Application No. PCT/US2021/065683, 3 pages.
Kidambi, Srivatsan, et al., "Cell Adhesion on Polyelectrolyte Multilayer Coated Polydimethylsiloxane Surfaces with Varying Topographies," Tissue Engineering, vol. 13, Nos. 2007, DOI: 10.1089/ten. 2006.0151, pp. 2105-2117.
Non-Final Office Action on U.S. Appl. No. 17/566,166 dated May 20, 2022.
Non-Final Office Action on U.S. Appl. No. 17/566,179 dated Jun. 14, 2022.

(Continued)

Primary Examiner — Kara D Johnson
(74) Attorney, Agent, or Firm — Foley & Lardner LLP

(57) ABSTRACT

The present disclosure provides methods of evaluating a therapeutic agent for cancer, and methods of cancer treatment.

22 Claims, 14 Drawing Sheets

(56) References Cited

OTHER PUBLICATIONS

Notice of Allowance on U.S. Appl. No. 17/566,179 dated Aug. 16, 2022.
Richert et al., "PH dependent growth of poly(L-lysine)/poly(L-glutamic) acid multilayer films and their cell adhesion properties," Surface Science Oct. 2004; 570(1-2): 13-29.
Takenaka, Chiemi, "Controlled Growth and the Maintenance of Human Pluripotent Stem Cells by Cultivation with Defined Medium on Extracellular Matrix-Coated Micropatterned Dishes," 2015, PLOS ONE, 10(6): e0129855: 1-13.
Trantidou, Tatiana, et al., "Hydrophilic surface modification of PDMS for droplet microfluidics using a simple, quick, and robust method via PVA deposition," 2017, Microsystems & Nanoengineering, 3:16091 (Year: 2017).
Tsai, Hsuan-Ang, et al., "Selection, Enrichment, and Maintenance of Self-Renewal Liver Stem/Progenitor Cells Utilizing Polypeptide Polyelectrolyte Multilayer Films," Biomacromolecules 2010, vol. 11, pp. 994-1001.
Tsai, Hsuan-Ang, et al., "Use of Surface Properties to Control the Growth and Differentiation of Mouse Fetal Liver Stem/Progenitor Cell Colonies," Biomacromolecules 2012, American Chemical Society, vol. 13, pp. 3483-3493.
Tu, et al., "Surface modification of poly(dimethysiloxane) and its applications in microfluidics-based biological analysis", Rev Anal Chem 2012: 31(3-4):177-192.
Written Opinion of the International Searching Authority dated Apr. 29, 2022 issued in International Application No. PCT/US2021/065694, 5 pages.
Written Opinion of the International Searching Authority dated May 2, 2022 issued in International Application No. PCT/US2021/065683, 5 pages.
Wu, Dapeng, et al., "Multilayer poly(vinyl alcohol)-adsorbed coating on poly(dimethylsiloxane) microfluidic chips for biopolymer separation," Electrophoresis, 2005, vol. 26, pp. 211-218.
Daverey, Amita, et al., "Breast Cancer/Stromal Cells Coculture on Polyelectrolyte Films Emulates Tumor Stages and miRNA Profiles of Clinical Samples," Langmuir 31, 2015, pp. 9991-10001.
International Search Report dated Jan. 27, 2023 issued in International Application No. PCT/US2022/045549, 5 pages.
Dromard, et al., "Human adipose derived stoma/stem cells grow in serum-free medium as floating spheres," 2011, Experimental Cell Research, 317(6): 770-780.
Non-Final Office Action on U.S. Appl. No. 17/566,166 dated Mar. 30, 2023.
Song, et al., "Dependence of Spreading and Differentiation of Mesenchymal Stem Cells on Micropatterned Surface Area," 2011, Journal of Nanomaterials, 2011: 265251.

\* cited by examiner

FIG. 1A          FIG. 1B          FIG. 1C
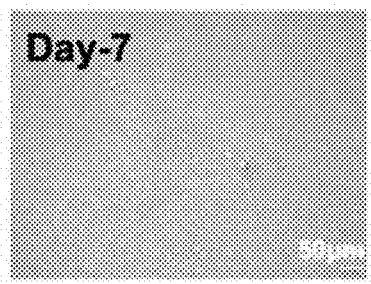 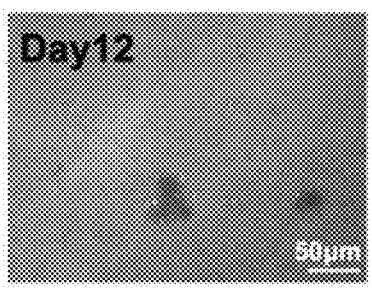 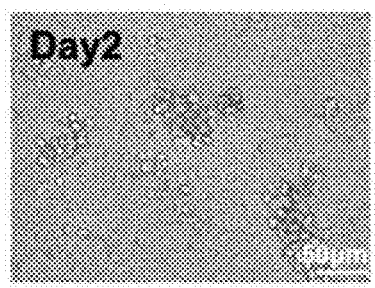
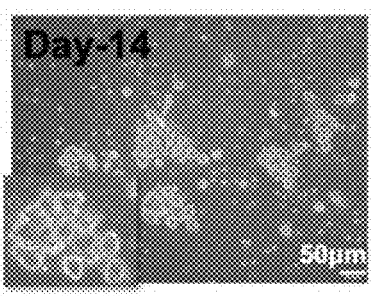 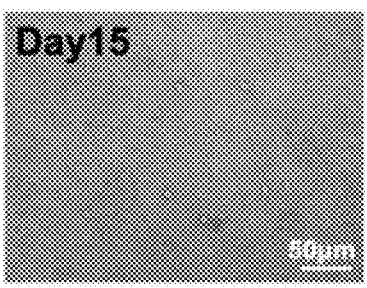 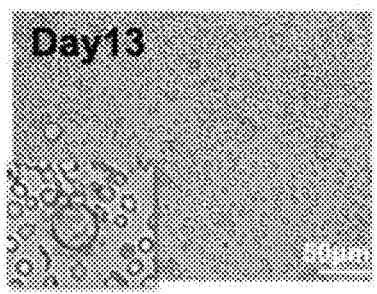
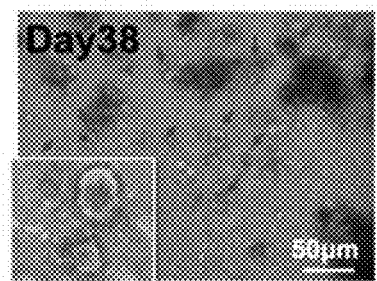 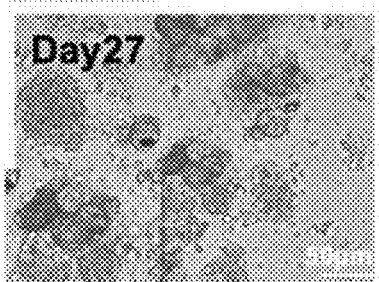

CELL CULTURE SUBSTRATES, METHODS AND USES THEREOF

CROSS-REFERENCE TO RELATED APPLICATIONS

This application is a continuation-in-part of U.S. patent application Ser. No. 17/566,179, filed Dec. 31, 2021, which claims priority to and the benefit of U.S. Provisional Patent Application No. 63/132,934, filed Dec. 31, 2020 and U.S. Provisional Patent Application No. 63/252,268, filed Oct. 5, 2021, the disclosure of which is hereby incorporated herein by reference in its entirety.

BACKGROUND OF THE INVENTION

The interest in 3D spheroid models is growing among researchers, from basic science to preclinical drug discovery applications, including studies in tumor biology, neurodegenerative diseases, and drug toxicity. Three-dimensional (3D) cell culture methods are increasingly used to generate complex tissue or tumor models.

There is a lot of variation in the spheroids formed using 3D cell culture methods and products available on the market, and this may impact their read-out. For instance, the widely used non-adherent techniques for 3D cell culture, including Ultra Low Attachment (ULA) plate and hanging drop method, have not proven suitable because these methods usually generate spheroids via cell agglomeration. Such spheroids generally maintain their original heterogeneity and harbor multiple cells with various characteristics, requiring a better understanding of cellular heterogeneity. When tens-of-thousands cells are aggregated into a spheroid (i.e., a mass with spherical shape), an extensive central necrotic core forms over a few hours due to the lack of nutrient and oxygen penetration beyond a 200 μm depth, and thus hinders cell proliferation. Extended central necrosis is a rare phenomenon in real cancers. Standardizing spheroid formation is critical to generating uniform 3D cell culture and obtaining reproducible results from spheroid-based assays and drug screening.

Immunotherapy has transformed the treatment of metastatic melanoma and other cancers, allowing a new avenue of therapeutic options and prolonging lives of many patients. Unfortunately, while immunotherapy is highly effective in some patients, it does not work for every patient and there are no available tests to determine whether or not a patient will respond to immunotherapy before treatment begins. A solution to this problem is to reliably generate a personalized ex vivo tumor model for evaluation of an immunotherapy to improve therapeutic quality and outcomes.

Currently, technologies and methods to reliably culture CTCs from most patients remain a challenge. Therefore, there is a need for the development of improved method that can reliably generate 3D cell cultures from CTCs retrieved from a blood sample of a cancer patient.

SUMMARY OF THE INVENTION

The present disclosure provides a cell culture substrate useful for preparing cell culture, in particular, 3D cell culture. The cell culture substrate described herein comprises a surface comprising polyelectrolyte multilayers (PEMs) and optionally an absorbent polymer. In some embodiments, the surface described herein comprises PEMs. In some embodiments, the surface described herein comprises PEMs and an absorbent polymer. The cell culture substrate disclosed herein comprises a support made of any suitable materials such as silicon, plastics, glass, elastomer and the like. In certain embodiments, the cell culture article comprises a support made of an elastomer. The elastomer described herein may be a silicone elastomer. In some embodiments, the silicone elastomer is polydimethylsiloxane (PDMS).

The present disclosure also relates to uses of the cell cultures (e.g. cancer cell cultures) described herein for in vitro drug screening, and for evaluating a therapeutic agent for cancer. Methods of cancer treatment are also provided.

Accordingly, one aspect of the present disclosure provides a method of preparing cell cultures (e.g. 3D cultures), in which the method comprises the steps of: (a) providing a cell culture substrate having a surface comprising polyelectrolyte multilayers and optionally an absorbent polymer described herein; (b) seeding a plurality of cells on the surface, wherein the plurality of cancer cells is obtained from a fluid sample of a cancer patient; and (c) culturing the plurality of cancer cells under a suitable medium for a time sufficient to produce cell cultures, wherein the cell cultures comprise 3D cell cultures comprising a plurality of tumor spheroids adhered to the surface on the surface.

As described herein, the fluid sample may be serum, plasma, whole blood, urine or ascitic fluid. In some embodiments, the plurality of cells may comprise primary tumor cells, metastatic tumor cells and/or circulating tumor cells. In some embodiments, the plurality of cells may comprise circulating tumor cells, wherein said circulating tumor cells include cancer cells from a solid tumor.

The tumor spheroids described herein may be generated via single cell proliferation. In some embodiments, the tumor spheroids are semi-attached or loosely attached to the surface.

In some embodiments, the surface described herein comprises polyelectrolyte multilayers and an absorbent polymer. Exemplary absorbent polymer includes, but is not limited to, poly(vinyl alcohol) (PVA), poly(ethylene glycol) (PEG), PEG-acrylate, polyvinylpyrrolidone (PVP), polyethyleneimine (PEI), poly-L-lactide (PLLA), poly-D-lactide (PDLA), poly(L-lactide-co-D,L-lactide) (PLDLLA), poly(glycolic acid) (PGA), poly(lactic-co-glycolic acid) (PL-co-GA), poly(methyl methacrylate) (PMMA), poly(hydroxyethyl methacrylate) (p-HEMA), and derivatives thereof.

In some embodiments, the culture medium comprises a Rho-associated protein kinase (ROCK) inhibitor. In some embodiments, the ROCK inhibitor is of a structural formula having an isoquinoline, 4-amidopyridine, or 4-amidopyrrolopyridine scaffold.

In another aspect, the present disclosure provides a method of evaluating a therapeutic agent for cancer, in which the method comprises the step of: (a) preparing cell cultures (e.g. 3D cultures) according to the method described herein; (b) optionally incubating the cell cultures with a plurality of immune cells; (c) contacting the cell cultures with a therapeutic agent; (d) evaluating an effect of the therapeutic agent on the cell cultures; and (e) determining the cancer patient as responsive to the therapeutic agent when the therapeutic agent is effective on the cell cultures; or determining the cancer patient as non-responsive to the therapeutic agent when the therapeutic agent is not effective on the cell cultures.

In some embodiments, the immune cells described herein comprise autologous immune cells from peripheral blood of the cancer patient. In some embodiments, the autologous immune cells comprise autologous immune cells expanded ex vivo.

The therapeutic agent described herein may include, but are not limited to, chemotherapeutic drugs, an immune checkpoint inhibitor, a nucleic acid drug, a therapeutic cell composition, and a combination thereof.

In some embodiments, the therapeutic agent is an immune checkpoint inhibitor, and the cell cultures are incubated with a plurality of immune cells (e.g. autologous immune cells from peripheral blood). The immune checkpoint inhibitor described herein may be a PD-1 inhibitor, a PD-L1 inhibitor, or a CLTA-4 inhibitor. Examples of the immune checkpoint inhibitors may include, but are not limited to, nivolumab, pembrolizumab, cemiplimab, atezolizumab, avelumab, durvalumab, and ipilimumab.

In some embodiments, the therapeutic agent is a therapeutic cell composition. In some embodiments, the therapeutic cell composition described herein is T cells, natural killer (NK) or dendritic cells. In some embodiments, the therapeutic cell composition is chimeric antigen receptor T (CAR-T) cells or chimeric antigen receptor-natural killer (CAR-NK) cells.

In some embodiments, the therapeutic agent comprises one or more chemotherapeutic drugs. The one or more chemotherapeutic drugs described herein may be cytotoxic or cytostatic chemotherapeutic drugs.

In some embodiments, the therapeutic agent comprises a nucleic acid drug.

In some embodiments, the cell cultures (e.g. 3D cultures) may be in direct contact with an outermost layer of the polyelectrolyte multilayers described herein. The outermost layer may be a polycation or a polyanion. In some embodiments, the polycation may be poly(L-lysine) (PLL), poly(L-arginine) (PLA), poly(L-ornithine) (PLO) or poly(L-histidine) (PLH), or a combination thereof. In some embodiments, the polyanion may be poly(L-glutamic acid) (PLGA) or poly(L-aspartic acid) (PLAA). In some embodiments, the polyelectrolyte multilayers may comprise n bilayers of polycation and polyanion. In some embodiments, n is an integer number ranging from 1 to 30.

In another aspect, the present disclosure provides a method of treating a cancer, in which the method comprises the steps of: (a) evaluating a therapeutic agent for a cancer patient according to the method described herein; and (b) administering to the cancer patient responsive to the therapeutic agent a therapeutically effective amount of the therapeutic agent.

The therapeutic agent described herein may be one or more chemotherapeutic drugs, an immune checkpoint inhibitor, a nucleic acid drug, a therapeutic cell composition, or a combination thereof.

BRIEF DESCRIPTION OF THE DRAWINGS

FIGS. 1A-1C show representative time-dependent images of CTC cultures generated on the surface according to one embodiment of the present disclosure. (A) CTC cultures derived from CTCs obtained from a blood sample of a breast cancer patient were generated on the surface after culturing for 7 and 14 days; (B) CTC cultures derived from CTCs obtained from a blood sample of a head and neck squamous cell carcinoma (HNSCC) patient were generated on the surface after culturing for 12, 15 and 38 days; (C) CTC cultures derived from CTCs obtained from a blood sample of a colorectal cancer (CRC) patient were generated on the surface after culturing for 2, 13 and 27 days. Scale bar: 50 µm

DETAILED DESCRIPTION

Figure 2A:
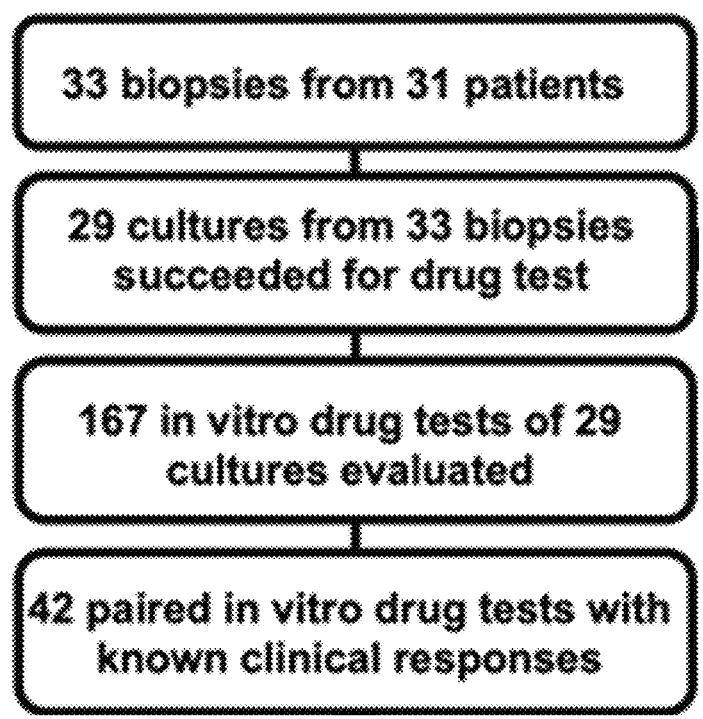
FIGS. 2A-2E show the correlation between drug sensitivity of CTC cultures with clinical response. (A) The overview flow chart of clinical sample distribution on the CTC-originated multi-cancer drug test. (B) The attempt of CTC-derived spheroids established from freshly collected blood specimen. Total 29 out of 33 specimens (88%) were successfully established CTC-spheroids initiated from numerous cancer types, including breast cancer (9/13), colon cancer (9/9), head/neck cancer (4/4), urothelial cancer (3/3), gastric cancer (1/1), and lung cancer (1/1). (C) Waterfall plot of the cell viability test based on clinical drug response of the paired CTC-spheroids tested on the cell culture platform of the invention. Gray bar indicated clinically resistant group, and white bar indicated clinically sensitive group. (D) The dot plot distribution of mean ±SEM on cell viability of drug tests from clinically resistant group and clinically sensitive group. Groups were compared using a t-test. Each dots/squares represent individual paired clinical responses. (E) The ROC curve of the clinical drug test results. The dotted line represents an $AUC_{ROC}$ of 0.5, which indicates no predictive value. CI, confidence interval.
Figure 2B:
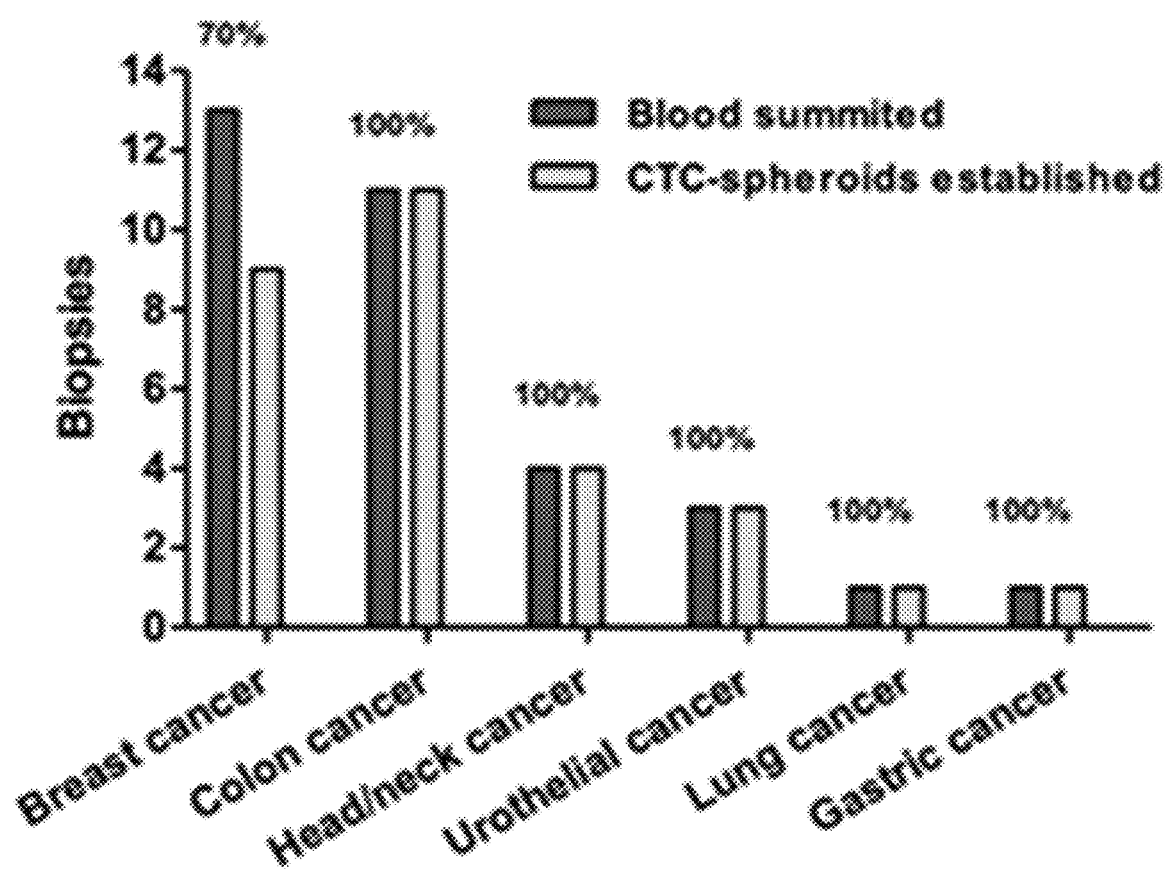
Figure 2C:
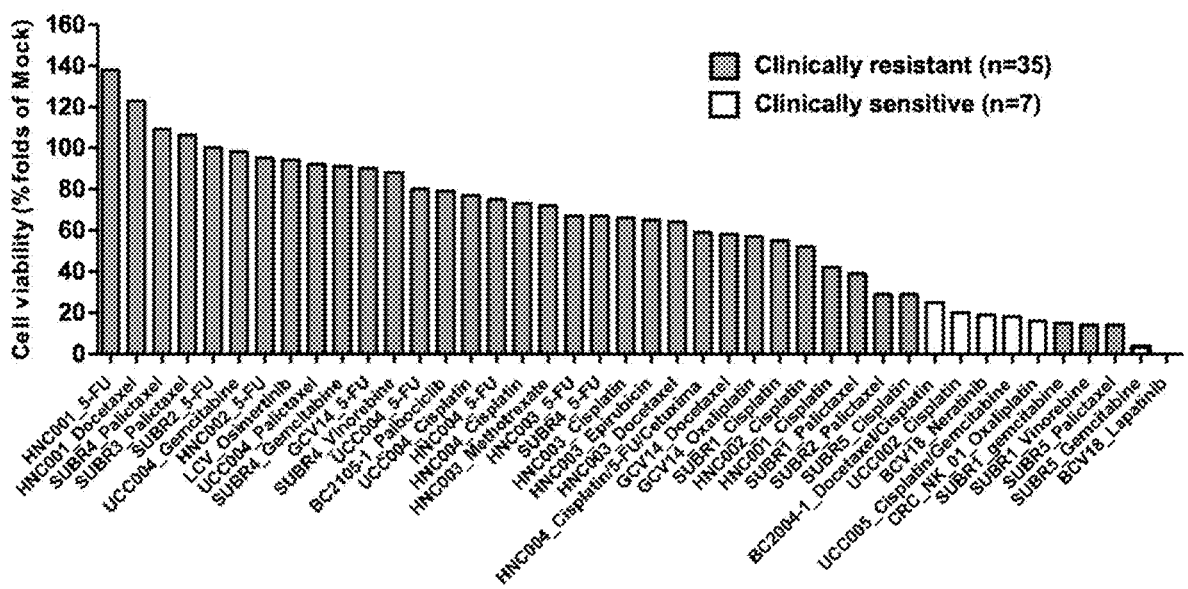

The present disclosure provides a cell culture substrate useful for preparing cell cultures, in particular, 3D cell cultures. The cell culture substrate described herein can induce the formation of 3D cell cultures, making it possible to form 3D cell cultures for certain primary cells such as CTCs that are difficult to propagate using other cell culture methods available on the market. Currently, technologies and methods to reliably culture CTCs from most patients remain a challenge. The present disclosure provides an improved method for allowing reliable and consistent expansion of CTCs. When CTC cultures are successfully established, they will provide valuable insights into the metastatic process and the therapeutic response of individual patients.

Cell Culture Substrates of the Invention

The cell culture substrate described herein comprises a surface comprising polyelectrolyte multilayers (PEMs) and optionally an absorbent polymer. In some embodiments, the surface described herein comprises PEMs. In some embodiments, the surface described herein comprises PEMs and an absorbent polymer. The cell culture substrate disclosed herein comprises a support made of any suitable materials such as silicon, plastics, glass, elastomer and the like. In certain embodiments, the cell culture article comprises a support made of an elastomer. The elastomer described herein may be a silicone elastomer. In some embodiments, the silicone elastomer is polydimethylsiloxane (PDMS).

PEMs disclosed herein comprise a plurality of alternating layers of oppositely charged polymers (i.e., polyelectrolytes). The oppositely charged polymers described herein comprise a combination of a positively charged polyelectrolyte (also referred to herein as a polycation) and a negatively charged polyelectrolyte (also referred to herein as a polyanion).

Exemplary polycations include, but are not limited to, poly(L-lysine) (PLL), poly(L-arginine) (PLA), poly(L-ornithine) (PLO), poly(L-histidine) (PLH), polyethyleneimine (PEI), poly[α-(4-aminobutyl)-L-glycolic acid] (PAGA), 2-(dimethylamino)ethyl methacrylate (DMAEMA), N,N-Diethylaminoethyl methacrylate (DEAEMA), and a combination thereof. In some instances, the polycation is PLL. In some instances, the polycation is PLO. In some instances, the polycation is PLH. In some instances, the polycation is PLA.

Exemplary polyanions include, but are not limited to, poly-L-glutamic acid (PLGA), poly-L-aspartic acid (PLAA), poly(acrylic acid), poly(methacrylic acid) (PMAA), poly(styrenesulfonic acid) (PSS), poly(N-isopropylacrylamide) (NIPAM), poly(2-acrylamido-2-methyl-1-propane sulfonic acid) (PAMPS), and a combination thereof. In some instances, the polyanionis PLGA. In some instances, the polyanion is PLAA.

Polyelectrolyte multilayers may be formed by depositing polycations and polyanions in an alternative fashion via layer-by-layer assembly. Polyelectrolyte multilayers described herein include at least one bilayer including a polycation layer and a polyanion layer.

In some embodiments, the PEMs may include from about 1 bilayers to about 100 bilayers. In some embodiments, the PEMs may include from about 1 bilayers about 50 bilayers. In some embodiments, the PEMs may include from about 1 bilayers to about 30 bilayers. In some embodiments, the PEMs may include from about 1 bilayers to about 20 bilayers. In some embodiments, the number of bilayers is 1, 2, 3, 4, 5, 6, 7, 8, 9, 10, 11, 12, 13, 14, 15, 16, 17, 18, 19 or 20. In some embodiments, the number of bilayers is in a range of 1-10, 1-8, 1-5, 3-20, 5-20, 10-20, 11-19, 12-18, 13-17, or 14-16. In some embodiments, the number of bilayers is 3. In some embodiments, the number of bilayers is 4. In some embodiments, the number of bilayers is 5. In some embodiments, the number of bilayers is 6. In some embodiments, the number of bilayers is 7. In some embodiments, the number of bilayers is 8. In some embodiments, the number of bilayers is 9. In some embodiments, the number of bilayers is 10. In some embodiments, the number of bilayers is 11. In some embodiments, the number of bilayers is 12. In some embodiments, the number of bilayers is 13. In some embodiments, the number of bilayers is 14. In some embodiments, the number of bilayers is 15. In some embodiments, the number of bilayers is 16. In some embodiments, the number of bilayers is 17. In some embodiments, the number of bilayers is 18. In some embodiments, the number of bilayers is 19. In some embodiments, the number of bilayers is 20.

In some embodiments, the polyelectrolyte multilayers described herein comprise one or more bilayers of positively charged polyelectrolyte(s) and negatively charged polyelectrolyte(s), in which the polycation is selected from PLL, PLO PLH, and PLA, and the polyanion is selected from PLGA and PLAA. In some embodiments, the number of sets ranges from 1 to 100, 3 to 60, from 3 to 50, or from 3 to 30. In some embodiments, the number of sets is greater than 3, 4, 5, 6, 7, 8, 9, 10, 11, 12, 13, 14, 15, 16, 17, 18, 19 or 20. In some embodiments, the number of sets is 3, 4, 5, 6, 7, 8, 9, 10, 11, 12, 13, 14, 15, 16, 17, 18, 19 or 20. In some embodiments, the number of sets is in a range of 1-10, 1-8, 1-5, 3-20, 5-20, 10-20, 11-19, 12-18, 13-17, or 14-16.

In some embodiments, the polyelectrolyte multilayers described herein comprise one or more bilayers of PLL and PLGA. In some embodiments, the number of bilayers of PLL and PLGA ranges from 1 to 100, 3 to 60, from 3 to 50, or from 3 to 30. In some embodiments, the number of bilayers is greater than 3, 4, 5, 6, 7, 8, 9, 10, 11, 12, 13, 14, 15, 16, 17, 18, 19 or 20. In some embodiments, the number of bilayers is 3, 4, 5, 6, 7, 8, 9, 10, 11, 12, 13, 14, 15, 16, 17, 18, 19 or 20. In some embodiments, the number of bilayers is in a range of 1-10, 1-8, 1-5, 3-20, 5-20, 10-20, 11-19, 12-18, 13-17, or 14-16.

In some embodiments, the polyelectrolyte multilayers described herein comprise one or more bilayers of PLO and PLGA. In some embodiments, the number of bilayers of PLO and PLGA ranges from 1 to 100, 3 to 60, from 3 to 50, or from 3 to 30. In some embodiments, the number of bilayers is greater than 3, 4, 5, 6, 7, 8, 9, 10, 11, 12, 13, 14, 15, 16, 17, 18, 19 or 20. In some embodiments, the number of bilayers is 3, 4, 5, 6, 7, 8, 9, 10, 11, 12, 13, 14, 15, 16, 17, 18, 19 or 20. In some embodiments, the number of bilayers is in a range of 1-10, 1-8, 1-5, 3-20, 5-20, 10-20, 11-19, 12-18, 13-17, or 14-16.

In some embodiments, the polyelectrolyte multilayers described herein comprise one or more bilayers of PLH and PLGA. In some embodiments, the number of bilayers of PLH and PLGA ranges from 1 to 100, 3 to 60, from 3 to 50, or from 3 to 30. In some embodiments, the number of bilayers is greater than 3, 4, 5, 6, 7, 8, 9, 10, 11, 12, 13, 14, 15, 16, 17, 18, 19 or 20. In some embodiments, the number of bilayers is 3, 4, 5, 6, 7, 8, 9, 10, 11, 12, 13, 14, 15, 16, 17, 18, 19 or 20. In some embodiments, the number of bilayers is in a range of 1-10, 1-8, 1-5, 3-20, 5-20, 10-20, 11-19, 12-18, 13-17, or 14-16.

In some embodiments, the polyelectrolyte multilayers described herein comprise one or more bilayers of PLA and PLGA. In some embodiments, the number of bilayers of PLA and PLGA ranges from 1 to 100, 3 to 60, from 3 to 50, or from 3 to 30. In some embodiments, the number of bilayers is greater than 3, 4, 5, 6, 7, 8, 9, 10, 11, 12, 13, 14, 15, 16, 17, 18, 19 or 20. In some embodiments, the number of bilayers is 3, 4, 5, 6, 7, 8, 9, 10, 11, 12, 13, 14, 15, 16, 17, 18, 19 or 20. In some embodiments, the number of bilayers is in a range of 1-10, 1-8, 1-5, 3-20, 5-20, 10-20, 11-19, 12-18, 13-17, or 14-16.

In some embodiments, the polyelectrolyte multilayers described herein comprise one or more bilayers of PLL and PLAA. In some embodiments, the number of bilayers of PLL and PLAA ranges from 1 to 100, 3 to 60, from 3 to 50, or from 3 to 30. In some embodiments, the number of bilayers is greater than 3, 4, 5, 6, 7, 8, 9, 10, 11, 12, 13, 14, 15, 16, 17, 18, 19 or 20. In some embodiments, the number of bilayers is 3, 4, 5, 6, 7, 8, 9, 10, 11, 12, 13, 14, 15, 16, 17, 18, 19 or 20. In some embodiments, the number of bilayers is in a range of 1-10, 1-8, 1-5, 3-20, 5-20, 10-20, 11-19, 12-18, 13-17, or 14-16.

In some embodiments, the polyelectrolyte multilayers described herein comprise one or more bilayers of PLO and PLAA. In some embodiments, the number of bilayers of PLO and PLAA ranges from 1 to 100, 3 to 60, from 3 to 50, or from 3 to 30. In some embodiments, the number of bilayers is greater than 3, 4, 5, 6, 7, 8, 9, 10, 11, 12, 13, 14, 15, 16, 17, 18, 19 or 20. In some embodiments, the number of bilayers is 3, 4, 5, 6, 7, 8, 9, 10, 11, 12, 13, 14, 15, 16, 17, 18, 19 or 20. In some embodiments, the number of bilayers is in a range of 1-10, 1-8, 1-5, 3-20, 5-20, 10-20, 11-19, 12-18, 13-17, or 14-16.

In some embodiments, the polyelectrolyte multilayers described herein comprise one or more bilayers of PLH and PLAA. In some embodiments, the number of bilayers of PLH and PLAA ranges from 1 to 100, 3 to 60, from 3 to 50, or from 3 to 30. In some embodiments, the number of bilayers is greater than 3, 4, 5, 6, 7, 8, 9, 10, 11, 12, 13, 14, 15, 16, 17, 18, 19 or 20. In some embodiments, the number of bilayers is 3, 4, 5, 6, 7, 8, 9, 10, 11, 12, 13, 14, 15, 16, 17, 18, 19 or 20. In some embodiments, the number of bilayers is in a range of 1-10, 1-8, 1-5, 3-20, 5-20, 10-20, 11-19, 12-18, 13-17, or 14-16.

In some embodiments, the polyelectrolyte multilayers described herein comprise one or more bilayers of PLA and PLAA. In some embodiments, the number of bilayers of PLA and PLAA ranges from 1 to 100, 3 to 60, from 3 to 50, or from 3 to 30. In some embodiments, the number of bilayers is greater than 3, 4, 5, 6, 7, 8, 9, 10, 11, 12, 13, 14, 15, 16, 17, 18, 19 or 20. In some embodiments, the number of bilayers is 3, 4, 5, 6, 7, 8, 9, 10, 11, 12, 13, 14, 15, 16, 17, 18, 19 or 20. In some embodiments, the number of bilayers is in a range of 1-10, 1-8, 1-5, 3-20, 5-20, 10-20, 11-19, 12-18, 13-17, or 14-16.

The thickness of the PEM as a thin film may be in a broad range, for example, in a range from about 30 nm to about 30 µm, or from about 100 nm to about 20 µm. In some embodiments, the thickness is about 100 nm to about 500 nm, about 500 nm to about 1 µm, or about 1 µm to about 10 µm. In some embodiments, the thickness is about 200, 400, 600, 800 nm, or any number in between. In some embodiments, the thickness is about 1, 5, 10, 15 or 20 µm, or any number in between.

A number of methodologies are available for characterizing PEMs. In some embodiments, the methodologies may comprise ellipsometry (thickness), quartz crystal microbalance with dissipation monitoring (mass adsorbed, viscoelasticity), contact angle analysis (surface energy), Fourier transform infrared spectroscopy (functional groups), X-ray photoelectron spectroscopy (chemical composition), scanning electron microscopy (surface structure), and atomic force microscopy (roughness/surface structure).

In some embodiments, PEMs may be deposited by pipetting polyanion or polycation solutions into/onto the dish, either as a mixture or sequentially.

In some embodiments, a PEM is formed on the surface by dip coating. In dip coating, the substrate is immersed in a polyelectrolyte solution for a set amount of time (usually 10-15 min), followed by multiple rinses and immersion in a second polyelectrolyte solution of opposite charge. This process is repeated until the desired number of layers is achieved.

In some embodiments, the PEM is formed on the surface by spray coating. In some embodiments, a polyelectrolyte may be sprayed onto the surface for 3-10 sec followed by a rest/draining period of 10-30 sec, washing of the surface with a water spray for 3-20 sec, an additional rest period of 10 sec, and repeating the cycle with a polyelectrolyte of opposite charge.

In some embodiments, the PEM is formed on the surface by spin coating. Spin coating is a highly controlled method for solution-based coating of a system. A typical spin coating procedure includes spin coating for 10-15 sec, rinsing at least once by "spin coating" water for 15-30 sec and repeating the procedure with the oppositely charged polyelectrolyte. The wash step may not be necessary in spin coating.

As described herein, the surface is hydrophilic if a contact angle for a water droplet on the surface is less than 90 degrees (the contact angle is defined as the angle passing through the drop interior). Embodiments include hydrophilic surfaces with a contact angle from 90 to 0 degrees; Artisans will immediately appreciate that all ranges and values between the explicitly stated bounds are contemplated, with, e.g., any of the following being available as an upper or lower limit: 90, 80, 70, 60, 50, 40, 30, 20, 10, 5, 2, 0 degrees.

In some embodiments, the substrate described herein comprises (polyanion/polycation)$_n$, wherein the polyanion/polycation is selected from PLGA/PLL, PLAA/PLL, PLGA/PLA, PLAA/PLA, PLGA/PLO, PLAA/PLO, PLGA/PLH and PLAA/PLH, and n is an integer number ranging from 1 to 20, optionally 1, 2, 3, 4, 5, 6, 7, 8, 9, 10, 11, 12, 13, 14, 15, 16, 17, 18, 19, 20. In some embodiments, n is in a range of 1-10, 1-8, 1-5, 3-20, 5-20, 10-20, 11-19, 12-18, 13-17, or 14-16.

In some embodiments, the substrate described herein comprises (polycation/polyanion)$_n$, wherein the polycation/polyanion is selected from PLL/PLGA, PLL/PLAA, PLA/PLGA, PLA/PLAA, PLO/PLGA, PLO/PLAA, PLH/PLGA and PLH/PLAA. In some embodiments, n is in a range of 1-10, 1-8, 1-5, 3-20, 5-20, 10-20, 11-19, 12-18, 13-17, or 14-16.

In some embodiments, the substrate described herein polycation (polyanion/polycation)$_n$, wherein the polyanion/polycation is selected from PLGA/PLL, PLAA/PLL, PLGA/PLA, PLAA/PLA, PLGA/PLO, PLAA/PLO, PLGA/PLH and PLAA/PLH. In some embodiments, n is in a range of 1-10, 1-8, 1-5, 3-20, 5-20, 10-20, 11-19, 12-18, 13-17, or 14-16.

In some embodiments, the substrate described herein polyanion (polycation/polyanion)$_n$, wherein the polycation/polyanion is selected from PLL/PLGA, PLL/PLAA, PLA/PLGA, PLA/PLAA, PLO/PLGA, PLO/PLAA, PLH/PLGA and PLH/PLAA. In some embodiments, n is in a range of 1-10, 1-8, 1-5, 3-20, 5-20, 10-20, 11-19, 12-18, 13-17, or 14-16.

In some embodiments, the surface of the cell culture substrate further comprises an absorbent polymer. The absorbent polymer described herein is a hydrophilic absorbent polymer A non-limiting list of absorbent polymers that may be used with the present invention includes hydrophilic and biocompatible grades of the following polymers and their derivatives: poly(vinyl alcohol) (PVA), ethylene vinyl alcohol co-polymers (typically non-biodegradable materials which degree of hydrophilicity depends on distribution of ethylene (hydrophobic) and vinyl alcohol (hydrophilic) groups), co-polymers of polyvinyl alcohol and ethylene vinyl alcohol, polyacrylate compositions, polyurethane compositions, poly(ethylene glycol) (PEG), otherwise known as poly(oxyethylene) (POE) and poly(ethylene oxide) (PEO), and its derivatives including but not limited to polyethylene glycol methacrylate (PEGMA), polyethylene glycol dimethacrylate (PEGDMA) and polyethylene glycol diacrylate (PEGDA); nitrogen-containing materials such as polyacrylamide (without acrylamide toxic residuals), polyvinylpyrrolidone, polyvinylamine, and polyethyleneimine; electrically charged materials such as poly(lactic acid) also known as polylactide in various forms (e.g. poly-L-lactide (PLLA) and its derivatives, poly-D-lactide (PDLA) and its derivatives, poly(L-lactide-co-D,L-lactide) (PLDLLA) and its derivatives), poly(glycolic acid) (PGA) also known as polyglycolide, co-polymers of lactic acid and glycolic acid poly(lactic-co-glycolic acid) (PL-co-GA), co-polymers of PLA and/or PGA with PEG; polymethacrylic acid; poly (hydroxyethyl methacrylate) (poly-HEMA), among other absorbent, hydrophilic and biocompatible materials known in the art.

In some embodiments, the absorbent polymer is selected from the group consisting of poly(vinyl alcohol) (PVA), copolymers of ethylene vinyl alcohol, copolymers of polyvinyl alcohol and ethylene vinyl alcohol, polyacrylate compositions, polyurethane compositions, poly(ethylene glycol) (PEG), PEG-acrylate, polyethylene glycol methacrylate (PEGMA), polyethylene glycol dimethacrylate (PEGDMA), polyethylene glycol diacrylate (PEGDA), polyacrylamide (PAM), polyvinylpyrrolidone (PVP), polyvinylamine (PVAm), polyethyleneimine (PEI), poly-L-lactide (PLLA), poly-D-lactide (PDLA), poly(L-lactide-co-D,L-lactide) (PLDLLA), poly(glycolic acid) (PGA), poly(lactic-co-glycolic acid) (PL-co-GA), poly(methyl methacrylate) (PMMA) and poly(hydroxyethyl methacrylate) (p-HEMA).

In some embodiments, the absorbent polymer is selected from the group consisting of PVA, PEG, PEG-acrylate, polylactide, PMMA, p-HEMA, a combination or a derivative thereof. In some embodiments, the absorbent polymer is PVA or a derivative thereof. In some embodiments, the absorbent polymer is PEG or PEG-acrylate such as PEGMA, PEGDMA or PEGDA. In some embodiments, the absorbent polymer is polylactide or a derivative such as PLLA, PDLA or PLDLLA. In some embodiments, the absorbent polymer is PGA or a derivative such as PLGA. In some embodiments, the absorbent polymer is PMAA or a derivative such as pHEMA.

In some embodiments, the absorbent polymer has an average molecular weight of from about 2,500 g/mol to about 200,000 g/mol. In some cases, the average molecular weight of the hydrophilic polymer is from about 5,000 g/mol to about 175,000 g/mol, from about 5,000 g/mol to about 150,000 g/mol, from about 5,000 g/mol to about 125,000 g/mol, from about 5,000 g/mol to about 100,000 g/mol, from about 5,000 g/mol to about 75,000 g/mol, from about 5,000 g/mol to about 50,000 g/mol, from about 5,000 g/mol to about 25,000 g/mol, from about 5,000 g/mol to about 10,000 g/mol, from about 10,000 g/mol to about 175,000 g/mol, from about 10,000 g/mol to about 150,000 g/mol, from about 10,000 g/mol to about 125,000 g/mol, from about 10,000 g/mol to about 100,000 g/mol, from about 10,000 g/mol to about 75,000 g/mol, from about 10,000 g/mol to about 50,000 g/mol, from about 10,000 g/mol to about 25,000 g/mol, from about 20,000 g/mol to about 150,000 g/mol, or from about 50,000 g/mol to about 150,000 g/mol.

In some instances, the absorbent polymer is deposited directly onto the surface of the cell culture substrate. In some instances, the hydrophilic polymer is deposited indirectly onto the surface of the cell culture substrate. In some cases, one or more additional layers (e.g., 1, 2, 3, 4, 5, or more layers) are formed between the hydrophilic polymer layer and the surface of the substrate. In some cases, one additional layer (also referred to herein as the innermost layer) is formed between the absorbent polymer layer and the support of the substrate.

In certain embodiments, the volume of the absorbent polymer (e.g. PVA or PEG) is from about 0.01% to about 10% of the total volume of the surface coating. In some instances, the absorbent polymer is from about 0.01% to about 9% v/v, from about 0.01% to about 8% v/v, from about 0.01% to about 7% v/v, from about 0.01% to about 6% v/v, from about 0.01% to about 5% v/v, from about 0.01% to about 4% v/v, from about 0.01% to about 3% v/v, from about 0.01% to about 2% v/v, from about 0.01% to about 1% v/v, from about 0.1% to about 10% v/v, from about 0.1% to about 9% v/v, from about 0.1% to about 8% v/v, from about 0.1% to about 7% v/v, from about 0.1% to about 6% v/v, from about 0.1% to about 5% v/v, from about 0.1% to about 4% v/v, from about 0.1% to about 3% v/v, from about 1% to about 10% v/v, from about 1% to about 9% v/v, from about 1% to about 8% v/v, from about 1% to about 7% v/v, from about 1% to about 6% v/v, from about 1% to about 5% v/v, from about 1% to about 4% v/v, from about 2% to about 10% v/v, or from about 5% to about 10% v/v, of the total volume of the surface coating.

In some instances, the weight of the absorbent polymer (e.g. PVA or PEG) per total weight of the surface coating is from about 1% to about 50%. In some instances, the weight of the absorbent polymer per total weight of the surface coating is from about 1% to about 10%, 20%, 30% or 40%.

In some embodiments, the substrate further comprises a filler. In some instances, the filler comprises a mineral filler such as but not limited to silica, alumina, calcium carbonate, or silicone resin.

Each of polycations and polyanions described herein may be dissolved in an aqueous solution for use in the present disclosure. The aqueous solution is free, or substantially free, of organic solvents. It will be understood that some minor amounts of organic solvents may be present in the aqueous solution, for example as a result some organic solvent remaining in the polymer after polymerization. As used herein, "substantially free," as it relates to an organic solvent in an aqueous solution, means that the aqueous solution comprises less than 1% of the organic solvent by weight. In many embodiments, the aqueous solution contains less than 0.8%, less than 0.5%, less than 0.2% or less that 0.1% of an organic solvent.

Each of polycations and polyanions may be dissolved in an aqueous solution at any suitable concentration for the purposes of coating.

The cell culture substrate disclosed herein comprises a support made of any suitable materials such as silicon, plastics, glass, elastomer and the like. In certain embodiments, the cell culture article comprises a support made of an elastomer. The elastomer described herein may be a silicone elastomer. In some embodiments, the silicone elastomer is polydimethylsiloxane (PDMS). In certain embodiments, the cell culture article comprises a support made of glass material such as soda-lime glass, pyrex glass, vycor glass, quartz glass. In certain embodiments, the cell culture article comprises a support made of plastics or polymers such as polyethylene, polypropylene, polymethylpentene, cyclic olefin polymer, cyclic olefin copolymer, polyvinyl chloride, polyurethane, polyester, polyamide, ethylene-vinyl acetate copolymer, ethylene-vinyl alcohol copolymer, ethylene-acrylic acid copolymer, ethylene-methyl acrylate copolymer, ethylene-methacrylic acid copolymer, ethylene-methyl methacrylate copolymer, polyacrylic acid, polymethacrylic acid, methyl polyacrylate, and methyl polymethacrylate, or derivatives of these or the like. In certain embodiments, the cell culture article comprises a support made of a material comprising at least one of polystyrene, polyethylene terephthalate, polycarbonate, polyvinylpyrrolidone, polybutadiene, polyvinylchloride, polyethylene oxide, polypyrroles, and polypropylene oxide.

The cell culture substrate disclosed herein enable not only cell attachment and growth, but also the viable harvest of cultured cells (e.g. 3D cell culture). According to some embodiments of the present disclosure, the cell culture substrate can be used to harvest viable cells, including between 80% to 100% viable, or about 85% to about 99% viable, or about 90% to about 99% viable. For example, of the cells that are harvested, at least 80% are viable, at least 85% are viable, at least 90% are viable, at least 91% are viable, at least 92% are viable, at least 93% are viable, at least 94% are viable, at least 95% are viable, at least 96% are viable, at least 97% are viable, at least 98% are viable, or at least 99% are viable. In some embodiments, cells can be released from the cell culture systems with or without using a cell dissociation enzyme, for example, trypsin, TrypLE, or Accutase.

Methods and Uses Thereof

1) Method of Preparing Cell Cultures

In one aspect, the present disclosure provides a method of preparing cell cultures using the cell culture substrate of the present disclosure. The method disclosed herein comprises the steps of: (a) providing a cell culture substrate having a surface comprising polyelectrolyte multilayers and optionally an absorbent polymer described herein; (b) seeding a plurality of cells on the surface; and (c) culturing the plurality of cells under a suitable medium for a time sufficient to produce cell cultures on the surface. In preferred embodiments, the cell cultures are adhered to the surface. In some embodiments, the cell cultures comprise three dimensional (3D) cell cultures. The 3D cell cultures may be in a form of spheroids. In some embodiments, the spheroids described herein are generated via single cell proliferation. In some embodiments, the cell cultures comprise one or more single-cell derived spheroids. In preferred embodiments, the single-cell-derived spheroids are adhered to the surface. In some embodiments, the single-cell-derived spheroids are semi-attached or loosely attached to the surface. In some embodiments, seeding a plurality of cells in step (b) comprises plating cells at a density of between one cell and 10 cells per cm$^2$ on the surface. In some embodiments, seeding a plurality of cells in step (b) comprises plating cells at a density of between 10 cells and 100 cells per cm$^2$ on the surface. In some embodiments, seeding a plurality of cells in step (b) comprises plating cells at a density of between 100 cells and 1000 cells per cm$^2$ on the substrate surface. In some embodiments, seeding a plurality of cells in step (b) comprises plating cells at a density of between 200 cells and 5000 cells per cm$^2$ on the substrate surface.

In some embodiments, the cells are cultured for a period of 2-8 days (e.g., 2, 3, 4, 5, 6, 7, or 8 days). In other embodiments, the cells are cultured for a period of 7-14 days (e.g., 7, 8, 9, 10, 11, 12, 13, or 14 days). In other embodiments, the cells are cultured for a period of 1-4 weeks (e.g., 1, 2, 3, or 4 weeks). Any suitable culture medium can be employed in the methods of exemplary embodiments. Exemplary culture medium includes, but is not limited to, Dulbecco's modified Eagle's medium (DMEM), epidermal growth factor (EGF) and/or basic fibroblast growth factor (bFGF), a mixture of Dulbecco's modified Eagle's medium (DMEM), supplemented with B27 supplement, epidermal growth factor (EGF) and basic fibroblast growth factor (bFGF).

In other embodiments, the plurality of cells are cancer cells. In other embodiments, the cancer cells comprise CTCs. In preferred embodiments, the medium for culturing CTCs may comprise epidermal growth factor (EGF), basic fibroblast growth factor (bFGF, or FGF2), additional growth factors such as fibroblast growth factor-10 (FGF10), granulocyte macrophage colony-stimulating factor (GM-CSF), insulin and insulin-like growth factor 1 (IGF-1). In some examples, R-spondin 1 protein may be included to sustain survival and growth of epithelial cells through WNT/β-catenin signaling. In some embodiments, when serum-free culture medium is used, B27 and N2 supplements may be added with or without insulin, transferrin and selenium (ITS) supplementation. In some embodiments, small molecule inhibitors for specific signaling pathways may be included in the medium for promoting CTC growth. For examples, A83-01 and ALX-270-445 (ALK5 Inhibitor II) may specifically inhibit the function of TGFβ type 1 receptor kinase (ALK5), thus prevent epithelial to mesenchymal transition and promote CTC survival and proliferation. SB202190, a p38 MAPK inhibitor, may prevent apoptosis due to p38 activation. In some embodiments, the culture medium may comprise a Rho-associated protein kinase (ROCK) inhibitor. The ROCK inhibitor described herein may be of a structural formula having an isoquinoline, 4-amidopyridine or 4-amidopyrrolopyridine scaffold. In some embodiments, the ROCK inhibitor is an isoquinoline-based ROCK inhibitor such as Fasudil, hydroxyfasudil, H-1152P, Ripasudil or a derivative thereof. In some embodiments, the ROCK inhibitor is a 4-amidopyridine-based ROCK inhibitor such as Y27632, Y32885, or a derivative thereof. In some embodiments, the ROCK inhibitor is a 4-amidopyrrolopyridine-based ROCK inhibitor such as Y30141, Y39983, or a derivative thereof. Structural formulae of Fasudil, hydroxyfasudil, H-1152P, Ripasudil, Y30141, Y39983, Y27632, and Y32885 are shown below.

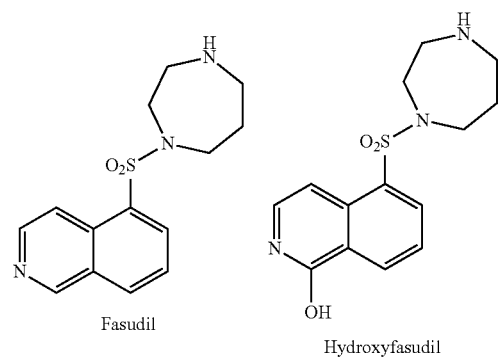

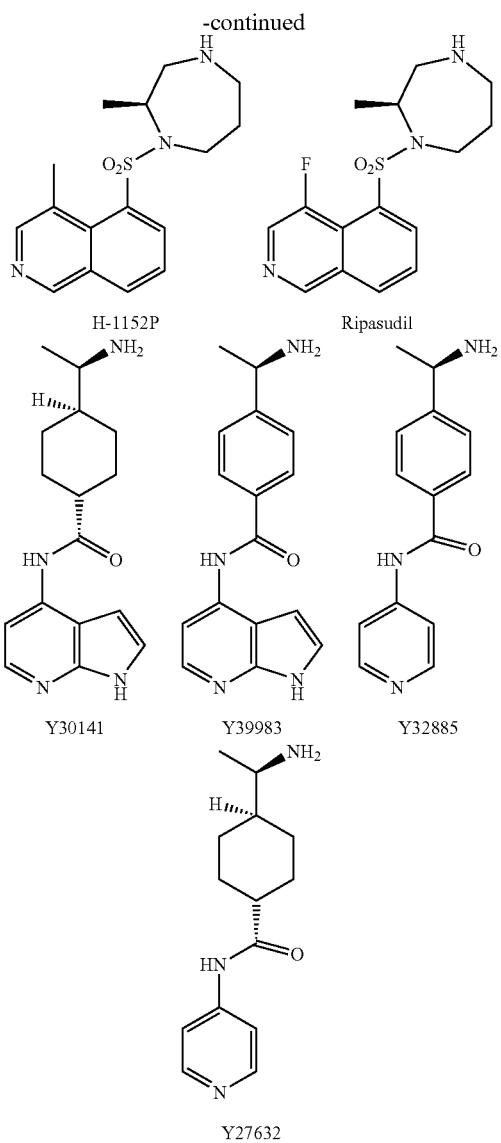

In some embodiments, the spheroids have an average diameter of from about 40 μm to about 200 μm. In some embodiments, the spheroids have an average diameter of from about 50 μm to about 150 μm. In some cases, the spheroids have an average diameter of from about 50 μm to about 120 μm, from about 50 μm to about 100 μm, from about 50 μm to about 80 μm, from about 50 μm to about 60 μm, from about 80 μm to about 150 μm, from about 80 μm to about 120 μm, from about 80 μm to about 100 μm, from about 100 nm to about 200 μm, from about 100 μm to about 150 μm, or from about 100 μm to about 120 μm.

In some cases, a spheroid described herein comprises from about 8 to about 1000 cells. In some cases, the spheroid comprises from about 8 to about 800 cells, from about 8 to about 500 cells, from about 8 to about 400 cells, from about 8 to about 300 cells, from about 8 to about 200 cells, from about 8 to about 100 cells, from about 10 to about 1000 cells, from about 10 to about 800 cells, from about 10 to about 500 cells, from about 10 to about 400 cells, from about 10 to about 300 cells, from about 10 to about 200 cells, from about 10 to about 100 cells, from about 50 to about 1000 cells, from about 50 to about 800 cells, from about 50 to about 500 cells, from about 50 to about 400 cells, from about 50 to about 300 cells, from about 50 to about 200 cells, from about 100 to about 1000 cells, from about 100 to about 800 cells, from about 100 to about 500 cells, from about 100 to about 400 cells, from about 100 to about 300 cells, from about 300 to about 1000 cells, from about 300 to about 800 cells, from about 300 to about 500 cells, from about 500 to about 1000 cells, or from about 500 to about 800 cells.

In some embodiments, the plurality of cells seeded on the surface are obtained from a biological sample of a cancer patient. In certain embodiments, the seeded cells described herein are isolated from human primary tumor sample. In some embodiments, the cancer cells can be obtained by mincing a primary tumor sample in a medium supplemented with serum; treating the minced primary tumor sample with an enzyme; and harvesting tumor spheroids from the enzyme treated sample. In some embodiments, the minced primary tumor sample is treated with the enzyme in an amount and/or for a time sufficient to yield a partial digestion of the minced primary tumor sample, and preferably wherein the treatment is for between 10 minutes and 60 minutes, and more preferably between 15 minutes and 45 minutes at a temperature of 25° C. to 39° C.

In some embodiments, the biological sample may be a fluid sample. In some embodiments, the fluid sample may be serum, plasma, whole blood, urine or ascitic fluid. In some embodiments, the fluid sample may comprise a patient's primary tumor cells, metastatic tumor cells and/or circulating tumor cells.

In certain embodiments, the seeded cells are isolated from a blood sample of a patient having a cancer. Several strategies are currently available for CTCs isolation. The enrichment is a crucial step when it comes to isolating viable CTCs from the rest of the blood constituents, such as platelets, red blood cells and white blood cells, allowing CTCs concentration and thus facilitating the detection process. The enrichment step can be performed through three different types of technologies: protein expression-based, physical property-based and function-based technologies. Examples of strategies for viable circulating tumor cell (CTC) isolation include, but are not limited to, RosetteSep®, CTC-iChip, Ficoll®, Ficoll-Pacque®, Lymphoprep®, Percoll®, Meta-Cell®, Parsortix®, Collagen adhesion matrix assay (CAM) and EPithelial ImmunoSPOT assay (EPISPOT).

Exemplary cancer described herein includes, but is not limited to, acute lymphatic cancer, acute myeloid leukemia, alveolar rhabdomycosarcoma, bone cancer, brain cancer, breast cancer, cancer of the anus, anal canal or anorectum cancer, cancer of the eye, cancer of the intrahepatic bile duct cancer, cancer of the joints, cancer of the neck, gallbladder or pleura cancer, cancer of the nose, nasal cavity or middle ear, cancer of the oral cavity, cancer of the vulva, chronic lymphatic leukemia, chronic myeloid cancer, colon cancer, esophageal cancer, cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum cancer, omentum and mesentary cancer, pharynx cancer, prostate cancer, rectal cancer, renal cancer, skin cancer, small intestine cancer, soft tissue cancer, stomach cancer, testicular cancer, thyroid cancer, ureter cancer, and urinary bladder cancer.

In some embodiments, the seeded cells may comprise tumor-associated cells. Exemplary tumor-associated cells include, but are not limited to, tumor cell clusters, tumor infiltrating lymphocytes (TILs), cancer associated macrophage-like cells (CAMLs), tumor-associated macrophages (TAMs), tumor-associated monocyte/macrophage lineage cells (MMLCs), cancer stem cells, tumor microemboli, tumor-associated stromal cells (TASC), tumor-associated myeloid cells (TAMCs), tumor-associated regulatory T cells (Treg), cancer-associated fibroblasts (CAFs), tumor-derived endothelial cells (TECs), tumor-associated neutrophils (TAN), tumor-associated platelets (TAP), tumor-associated immune cells (TAI), myeloid-derived suppressor cells (MDSC), and a combination thereof.

The spheroids described herein comprises a plurality of cultured cancer cells. In certain embodiments, the plurality of cultured cancer cells may be used for evaluating a therapeutic agent for a cancer patient.

In certain embodiments, the cancer cell cultures described herein comprise one or more cancer cell spheroids (e.g. tumor spheroids). The tumor spheroids described herein may be used for evaluating a therapeutic agent for cancer.

2) Method of Evaluating Therapeutic Agents

Another aspect of the present disclosure features a method for evaluating a therapeutic agent for a cancer patient. The method comprises the steps of: (a) preparing cell cultures (e.g. CTC cultures) according to the method described herein; (b) optionally incubating the cell cultures with a plurality of immune cells; (c) contacting the cell cultures with a therapeutic agent; (d) evaluating an effect of the therapeutic agent on the cell cultures; and (e) determining the cancer patient as responsive to the therapeutic agent when the therapeutic agent is effective on the cell cultures; or determining the cancer patient as non-responsive to the therapeutic agent when the therapeutic agent is not effective on the cell cultures.

In some embodiments, the effect of the therapeutic agent is analyzed by performing cell-based and/or biochemical assays based on luminescence and/or fluorescence. In some embodiments, the effect of the therapeutic agent is analyzed by performing luminescence-based cell viability assays. In some embodiments, the effect of the therapeutic agent may be analyzed by performing one or more assays to determine size, morphology, a physical property, a biological property, and/or a kinetic property of cells in the tumor spheroid. In some embodiments, the effect of the therapeutic agent may be further analyzed based on one or more assays to analyze the biochemical activity and/or the expression levels of one or more genes or one or more proteins in the tumor spheroids. Assay results may provide a treatment guideline for the cancer patient. In some embodiments, the plurality of immune cells described herein comprise autologous immune cells from peripheral blood. In some embodiments, the autologous immune cells comprise autologous immune cells expanded ex vivo. In some embodiments, the immune cells comprise autologous natural killer (NK) cells isolated from peripheral blood and expanded ex vivo. In other embodiments, the immune cells comprise allogenic natural killer (NK) cells isolated from a donor and expanded ex vivo. In other embodiments, the immune cells comprise natural killer (NK) cells differentiated from human induced pluripotent stem cells (iPSCs) or embryonic stem cells (ESCs) and expanded ex vivo. The step of incubating the tumor spheroid with a plurality of immune cells can form tumor cell-immune cell cocultures that may allow ex vivo recapitulation of the tumor microenvironment mimicking that occurring in vivo such that the effectiveness of a therapeutic agent, when administered in vivo, in treating cancer may be assessed.

Suitable therapeutic agents include, but are not limited to, a chemotherapeutic drug, an immune checkpoint inhibitor, a nucleic acid drug, a therapeutic cell composition, and a combination thereof.

In some embodiments, the therapeutic agent is a cytotoxic or cytostatic chemotherapeutic drug. The method described herein comprises a step of contacting the tumor spheroid with a cytotoxic or cytostatic chemotherapeutic drug in the presence or absence of a plurality of immune cells. The chemotherapeutic drug may be alkylating agents (such as cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil (5-FU), gemcitabine, methotrexate, cytosine arabinoside, fludarabine, and floxuridine), antimitotics (including taxanes such as paclitaxel and decetaxel and vinca alkaloids such as vincristine, vinblastine, vinorelbine, and vindesine), anthracyclines (including doxorubicin, daunorubicin, valrubicin, idarubicin, and epirubicin, as well as an actinomycin such as actinomycin D), cytotoxic antibiotics (including mitomycin, plicamycin, and bleomycin), topoisomerase inhibitors (including camptothecins such as camptothecin, irinotecan, and topotecan as well as derivatives of epipodophyllotoxins such as amsacrine, etoposide, etoposide phosphate, and teniposide), antibodies to vascular endothelial growth factor (VEGF) such as bevacizumab (AVASTIN®), other anti-VEGF compounds; anti-PD-1 (anti-programmed death-1) therapeutics such as antibodies or compounds (e.g., Nivolumab); thalidomide (THALOMID®) and derivatives thereof such as lenalidomide (REVLIMID®); endostatin; angiostatin; receptor tyrosine kinase (RTK) inhibitors such as sunitinib (SUTENT®); tyrosine kinase inhibitors such as sorafenib (Nexavar®), erlotinib (Tarceva®), pazopanib, axitinib, and lapatinib; transforming growth factor-α or transforming growth factor-β inhibitors, and antibodies to the epidermal growth factor receptor such as panitumumab (VECTIBIX®) and cetuximab (ERBITUX®).

In some embodiments, the therapeutic agent is an immune checkpoint inhibitor. The method described herein comprises a step of contacting the tumor spheroid with an immune checkpoint inhibitor in the presence of a plurality of immune cells. The immune checkpoint inhibitor may be CD137, CD134, PD-1, KIR, LAG-3, PD-L1, PDL2, CTLA-4, B7.1, B7.2, B7-DC, B7-H1, B7-H2, B7-H3, B7-H4, B7-H5, B7-H6, B7-H7, BTLA, LIGHT, HVEM, GALS, TIM-3, TIGHT, VISTA, 2B4, CGEN-15049, CHK 1, CHK2, A2aR, TGF-β, PI3Kγ, GITR, ICOS, IDO, TLR, IL-2R, IL-10, PVRIG, CCRY, OX-40, CD160, CD20, CD52, CD47, CD73, CD27-CD70, CD40, and a combination thereof. In some embodiments, the therapeutic agent is an immune checkpoint inhibitor selected from PD-1 inhibitor, a PD-L1 inhibitor, and a CLTA-4 inhibitor. The immune checkpoint inhibitor described herein is selected from the group consisting of group consisting of nivolumab, pembrolizumab, cemiplimab, atezolizumab, avelumab, durvalumab, and ipilimumab.

In some embodiments, the therapeutic agent is a nucleic acid drug. The method described herein comprises a step of contacting the tumor spheroid with a nucleic acid drug in the presence or absence of a plurality of immune cells. The nucleic acid drug may be DNA, DNA plasmid, nDNA, mtDNA, gDNA, RNA, siRNA, miRNA, mRNA, piRNA, antisense RNA, snRNA, snoRNA, vRNA, and a combination thereof. In some embodiments, the therapeutic nucleic acid is a DNA plasmid comprising a nucleotide sequence encoding a gene selected from the group consisting of GM-CSF, IL-12, IL-6, IL-4, IL-12, TNF, IFNy, IFNa, and a combination thereof.

In some embodiments, the therapeutic agent is a therapeutic cell composition. The method described herein comprises a step of contacting the tumor spheroid with a therapeutic cell composition in the absence of a plurality of immune cells. Exemplary therapeutic cell compositions include, but are not limited to T cells, natural killer (NK) cells and dendritic cells, chimeric antigen receptor T (CAR-T) cells and chimeric antigen receptor-natural killer (CAR-NK) cells.

3) Method of Treating Cancer Using Immunotherapy

Another aspect of the present disclosure features a method for treating a cancer using immunotherapy for a cancer patient. The method comprises the steps of: (a) evaluating a therapeutic agent for the immunotherapy for a cancer patient according to the method described herein; and (b) administering to the cancer patient responsive to the therapeutic agent a therapeutically effective amount of the therapeutic agent.

In some embodiments, the therapeutic agent for the immunotherapy comprises an immune checkpoint inhibitor. In some embodiments, the therapeutic agent for the immunotherapy comprises a therapeutic cell composition. In some embodiments, the therapeutic agent for the immunotherapy comprises a nucleic acid drug. In some embodiments, the cancer patient is further administered with a cytotoxic or cytostatic chemotherapeutic drug.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described.

As used herein, the term "comprising" is intended to mean that the methods include the recited steps or elements, but do not exclude others. "Consisting essentially of" shall mean rendering the claims open only for the inclusion of steps or elements, which do not materially affect the basic and novel characteristics of the claimed methods. "Consisting of" shall mean excluding any element or step not specified in the claim. Embodiments defined by each of these transition terms are within the scope of this disclosure.

As used herein, the term "positively charged polyelectrolyte" encompasses a plurality of monomer units or a non-polymeric molecule that comprises two or more positive charges. In some instances, the positively charged polyelectrolyte also encompasses a plurality of monomer units or a non-polymeric molecule that comprise charge positive groups, charge neutral groups, or charge negative groups, with a net charge of being positive.

As used herein, the term "cationic polymer" encompasses a plurality of monomer units or a non-polymeric molecule. In some instances, the cationic polymer is a synthetic polymer. In other instances, the cationic polymer is a natural polymer.

As used herein, the term "cationic polypeptide" refers to a polypeptide comprising two or more positive charges. In some instances, the cationic polypeptide comprises positively charged amino acid residues, negatively charged residues, and polar residues but the net charge of the polypeptide is positive. In some cases, the cationic polypeptide is from 8 to 100 amino acids in length. In some cases, the cationic polypeptide is from 8 to 80, 8 to 50, 8 to 40, 8 to 30, 8 to 25, 8 to 20, 8 to 15, 10 to 100, 10 to 80, 10 to 50, 10 to 40, 10 to 30, 10 to 20, 20 to 100, 20 to 80, 20 to 50, 20 to 40, 20 to 30, 30 to 100, 30 to 80, 30 to 50, 40 to 100, 40 to 80, or 50 to 100 amino acids in length.

As used herein, the term "negatively charged polyelectrolyte" encompasses a plurality of monomer units or a non-polymeric molecule that comprises two or more negative charges. In some instances, the negatively charged polyelectrolyte also encompasses a plurality of monomer units or a non-polymeric molecule that comprise charge positive groups, charge neutral groups, or charge negative groups, with a net charge of being negative.

As used herein, the term "anionic polymer" encompasses a plurality of monomer units or a non-polymeric molecule. In some instances, the anionic polymer is a synthetic polymer. In other instances, the anionic polymer is a natural polymer.

As used herein, the term "anionic polypeptide" refers to a polypeptide comprising two or more negative charges. In some instances, the anionic polypeptide comprises positively charged amino acid residues, negatively charged residues, and polar residues but the net charge of the polypeptide is negative. In some cases, the anionic polypeptide is from 8 to 100 amino acids in length. In some cases, the anionic polypeptide is from 8 to 80, 8 to 50, 8 to 40, 8 to 30, 8 to 25, 8 to 20, 8 to 15, 10 to 100, 10 to 80, 10 to 50, 10 to 40, 10 to 30, 10 to 20, 20 to 100, 20 to 80, 20 to 50, 20 to 40, 20 to 30, 30 to 100, 30 to 80, 30 to 50, 40 to 100, 40 to 80, or 50 to 100 amino acids in length.

As used herein, the term "polymer" includes both homo- and copolymers, branched and unbranched, and natural or synthetic polymers.

As used herein, the term "tumor" refers to a neoplasm, i.e., an abnormal growth of cells or tissue and is understood to include benign, i.e., non-cancerous growths, and malignant; i.e., cancerous growths including primary or metastatic cancerous growths.

Examples of neoplasms include, but are not limited to, mesothelioma, lung cancer (e.g., small-cell lung cancer, non-small cell lung cancer), skin cancer (e.g., melanoma), stomach cancer, liver cancer, colorectal cancer, breast cancer, pancreatic cancer, prostate cancer, blood cancer, bone cancer, bone marrow cancer, and other cancers.

The term "tumor spheroid," or "tumor cell spheroid" as used herein, refers to an aggregation of tumor cells constituting a small mass, or lump of tumor cells. In some embodiments, tumor spheroids are less than about 3 cm, less than about 2 cm, less than about 1 cm, less than about 5 mm, less than about 2.5 mm, less than about 1 mm, less than about 100 µm, less than about 50 µm, less than about 25 µm, less than about 10 μm, or less than about 5 μm in diameter. In some embodiments, the tumor spheroids have a diameter of 10 μm to 500 μm. In some embodiments, the tumor spheroids have a diameter of 40 μm to 100 μm. In some embodiments, the tumor spheroids have a diameter of 40 μm to 70 μm.

As used herein, immune cells encompass neutrophils, eosinophils, basophils, mast cells, monocytes, macrophages, dendritic cells, natural killer cells, and lymphocytes (B cells and T cells).

EXAMPLES

These examples are provided for illustrative purposes only and not to limit the scope of the claims provided herein.

Example 1

Construction of the Surface of the Invention

For construction of a surface coating with polyelectrolyte multilayers, a plasma-treated tissue culture plate (TCP, polystyrene) was used for polycation/polyanion deposition. The plasma treatment is to expose the surface of TCP plate to an oxygen plasma. Oxygen plasma treatment generates radical species of surface silanol groups (Si—OH), alcoholic hydroxyls (C—OH), and carboxylic acids (COOH) on the surface and these species allow hydrogen bonding between the polyanion (or polyanion) and the activated TCP surface.

To build up polyelectrolyte multilayers, both polycation and polyanion were dissolved in Tris-HCl buffer (pH 7.4) and deposited onto TCP surface after rinsing with Tris-HCl buffer. Each layer of polycation or polyanion was deposited and incubated, followed by washing with Tris-HCl buffer. In some examples, the polycation is poly-L-lysine (PLL) and the polyanion is poly-L-glutamic acid (PLGA). In some examples, the polycation is PLO and the polyanion is PLGA. In some examples, the polycation is PLH and the polyanion is PLGA. In some examples, the polycation is PLA and the polyanion is PLGA. PLL (MW 150K-300K), PLGA (MW 50K-100K), PLO (0.01%) solution, PLH (MW 5K-25K), PLA (MW 15K-70K) are commercially available from Sigma-Aldrich (St. Louis, Mo., USA). Both polycation and polyanion are dissolved in Tris-HCl buffer (pH 7.4) and deposited onto the TCP plate after rinsing with Tris-HCl buffer. Each layer of polycation or polyanion is deposited and incubated for 10 min, followed by washing with Tris-HCl buffer 3 times for 2, 1, and 1 min. The PLL/PLGA, PLO/PLGA, PLH/PLGA and PLA/PLGA multilayer films can be fabricated by layer-by-layer self-assembly as follows.

In some examples, the polyelectrolyte multilayers are PLL/PLGA multilayers that can be constructed by sequentially depositing PLL and PLGA on a plate. Each depositing step comprises adding the PLL or PLGA solution to the plate surface, incubated for 10 min and washed 3 times for 2, 1, and 1 min. In one embodiment, the substrate composed of $(PLGA/PLL)_3$ is constructed. In one embodiment, the substrate coating composed of $(PLGA/PLL)_5$ is constructed. In one embodiment, the substrate composed of $(PLGA/PLL)_{10}$ is constructed. In one embodiment, the substrate composed of $(PLGA/PLA)_{15}$ is constructed.

In some examples, the polyelectrolyte multilayers are PLO/PLGA multilayers that can be constructed by sequentially depositing PLO and PLGA on a plate. Each depositing step comprises adding the PLO or PLGA solution to the plate surface, incubated for 10 min and washed 3 times for 2, 1, and 1 min. In one embodiment, the substrate composed of $(PLGA/PLO)_3$ is constructed. In one embodiment, the substrate coating composed of $(PLGA/PLO)_5$ is constructed. In one embodiment, the substrate composed of $(PLGA/PLO)_{10}$ is constructed. In one embodiment, the substrate composed of $(PLGA/PLO)_{15}$ is constructed.

In some examples, the polyelectrolyte multilayers are PLH/PLGA multilayers that can be constructed by sequentially depositing PLH and PLGA on a plate. Each depositing step comprises adding the PLH or PLGA solution to the plate surface, incubated for 10 min and washed 3 times for 2, 1, and 1 min. In one embodiment, the substrate composed of $(PLGA/PLH)_3$ is constructed. In one embodiment, the substrate coating composed of $(PLGA/PLH)_5$ is constructed. In one embodiment, the substrate composed of $(PLGA/PLH)_{10}$ is constructed. In one embodiment, the substrate composed of $(PLGA/PLH)_{15}$ is constructed.

In some examples, the polyelectrolyte multilayers are PLA/PLGA multilayers that can be constructed by sequentially depositing PLA and PLGA on a plate. Each depositing step comprises adding the PLA or PLGA solution to the plate surface, incubated for 10 min and washed 3 times for 2, 1, and 1 min. In one embodiment, the substrate composed of $(PLGA/PLA)_3$ is constructed. In one embodiment, the substrate coating composed of $(PLGA/PLA)_5$ is constructed. In one embodiment, the substrate composed of $(PLGA/PLA)_{10}$ is constructed. In one embodiment, the substrate composed of $(PLGA/PLA)_{15}$ is constructed.

Example 2

Comparison of Cell Culture Platforms for Spheroid Formation

In order to establish an ex vivo 3D model to facilitate clinical applications such as personalized drug testing, various culture platforms were evaluated. The Ultralow attachment (ULA) plate (Corning), as a suspension culture platform, enabled spheroid formation based on cell aggregation, resulting in a very low yield in spheroid formation. In our experiments, less than 1% in number of cells seeded and cultured on ULA plate could form spheroids. For comparison, a plate coated with layer-by-layer polyelectrolyte multilayers (PEM) was evaluated for ex vivo cultivation of spheroids. Using HCT116 colorectal cancer cell line as an example, 78.7±2.7% of cells seeded and cultured on the PEM-coated plate could proliferate and form cell spheroids after culturing for 5-7 days using DMEM complete medium whereas only 0.2±0.1% of cells seeded and cultured on ULA plate formed spheroids. To evaluate whether the culture medium effects spheroid formation on various culture platforms, a growth factors supplied serum-free medium (SPH medium) was used for spheroid formation test. Results showed that 62.2±2.3% of cells seeded and cultured on the PEM-coated culture plate could proliferate and form cell spheroids after culturing for 5-7 days whereas only 0.7±0.1% of cells seeded and cultured on ULA plate formed spheroids. Similar to ULA plate, a plate coated with poly-HEMA resulted in a low yield in spheroid formation. Matrigel, a commonly used embedded substrate for tissue-based cell culture, was also tested. The result showed the spheroids generated were embedded in the Matrigel, resulting in a difficulty in analyzing and imaging the spheroids as the image was blurry or out of focus.

Example 3

Formation of Viable Spheroids on the Culture Platform of the Invention

Liquid biopsy provides possibility to obtain real-time cancer specimen directly from blood. But the rarity of the circulating tumor cell (CTC) impaired the whole process for ex vivo application in clinical usage. Several papers have demonstrated the feasibility in using circulating tumor cells for individual drug screening or testing, but they barely provide a non-biased 3D cultured model for clinical application. In order to test the feasibility of the PEM-coated culture plate for rare cell expansion, very low density of HCT116 cells were seeded onto the surface of the PEM-coated culture plate and imaged under time-lapse microscope. A single cell showed semi-adhesion on the surface of the PEM-coated culture plate and continued proliferate to form a spheroid having a diameter of about 70 μm after 7 days. The single cell-derived spheroid on the PEM-coated culture plate may thus facilitate following clinical applications by taking advantage of rare cell samples. In addition, with higher density of cells seeded onto the surface of the PEM-coated culture plate, the cells remained growth to for spheroids from each single cells. But the cells undergo spheroid fusion when two spheroids closed enough to each other to form a bigger spheroid. To establish a 3D spheroid-based rare cell expansion technology for clinical utility, uniformity in spheroid size and viable spheroid maintenance are desired to eliminate potential bias during ex vivo testing. Total 300 cells were seeded onto the wells with the inventive surface coating in 96-well plate to test the uniformity of the spheroid size grown on the cell culture platform of the invention. The cells proliferated and formed spheroids. The size of spheroids were verified by Opera Phenix high content confocal screening system (Perkin Elmer). The average number of spheroids per well is 320±54 and the mean spheroid diameter of each well is 69±34 μm at day 5. The results demonstrated high spheroid formation ability and uniform spheroid size formed on the PEM-coated culture plate. The spheroids grown on either UL platform or the cell culture platform of the invention were isolated and stained with LIVE/DEAD assay (Invitrogen) to test the viability of the cells. The fluorescence intensity analysis of the EthD1 revealed significant higher dead spheroid cells cultured on UL platform in comparison with spheroids cultured on the cell culture platform of the invention. Furthermore, spheroids cultured on the PEM-coated culture plate showed high cell viability after freeze&-thaw cycle preservation, indicating positive cell survival after cryobanking process. In addition, a confocal microscope scanning revealed a tight cell-cell interaction in the spheroids cultured on the PEM-coated culture plate rather than a loose cell-cell contact in aggregated spheroid generated on ULA plate. The uniform and viable single cell-derived spheroid may thus facilitate clinical application such as personalized drug test.

Example 4

Patient-Derived Spheroids from Clinical Samples

To establish patient-derived spheroids for clinical utility, patient-derived specimens from tissue resection, core-needle biopsy, and phlebotomy blood draw were collected for ex vivo spheroid cultivation. In some examples, cancer cells were obtained from a tumor tissue. In some examples, cancer cells were obtained from blood samples. Viable CTCs can be isolated using the methods known in the arts. All the viable cells can be seeded onto the surface of the PEM-coated culture plate to generate patient-derived spheroids within 2 to 4 weeks. FIGS. 1A-1C illustrates representative time-dependent images of CTC cultures generated on the surface according to one embodiment of the present disclosure. (A) CTC cultures derived from CTCs in a blood sample of a breast cancer patient were generated on the surface after culturing for 7 and 14 days; (B) CTC cultures derived from CTCs in a blood sample of a head and neck squamous cell carcinoma (HNSCC) patient were generated on the surface after culturing for 12, 15 and 38 days; (C) CTC cultures derived from CTCs in a blood sample of a colorectal cancer (CRC) patient were generated on the surface after culturing for 2, 13 and 27 days. Scale bar: 50 μm Example 5

High Concordance between ex vivo Drug Tests on CTC-Derived Spheroids with Clinical Responses Patient-derived CTC cultures were successfully generated outside the patient's body from 33 blood specimens that were obtained from 31 cancer patients recruited in the study. The specimens were derived from the patient diagnosed with breast (n=13), colon (n=11), head&neck (n=4), urothelium (n=3), lung (n=1), and stomach (n=1) cancers. These blood specimens were collected and cultured on the surface of the cell culture platform of the invention.

The rate of successfully generating CTC cultures is calculated as 88% (29 out of 33 specimens). 4 specimens from patients with breast cancer have insufficient sample quantity for conducting drug tests.

We then examined the relevance between cell viability of each drug test in CTC cultures with clinical responses in patients. Total 167 ex vivo drug tests from the 29 CTC cultures were generated on the surface of the culture platform of the present disclosure. For comparison, 42 treatment results were acquired from paired clinical patients. Among 42 treatment results with known clinical responses, 35 CTC cultures with paired patient treatments were classified as clinically resistant group, and another 7 patient treatments were classified as clinically sensitive group based on their own treatment response described by physicians.

Figure 2D:
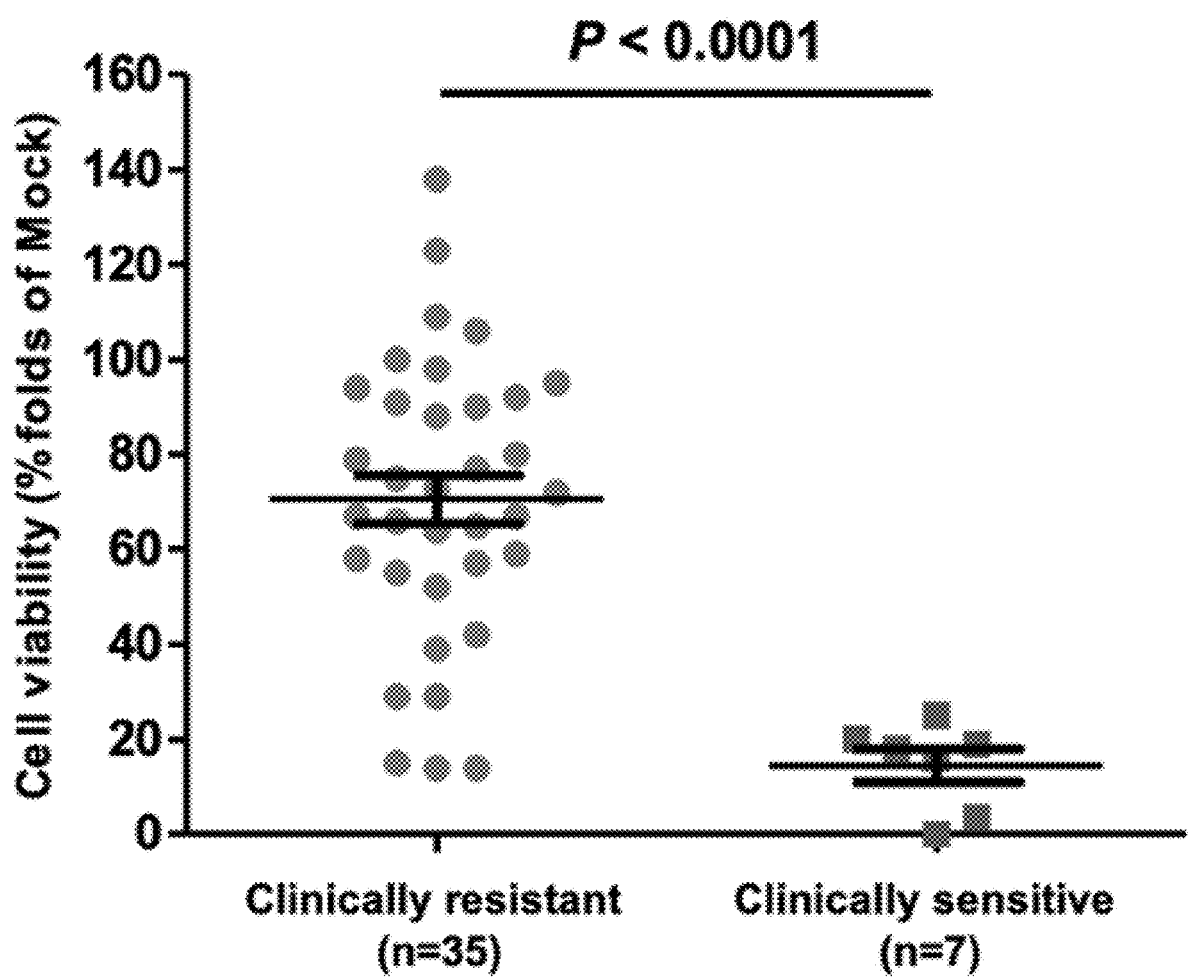
Figure 2E:
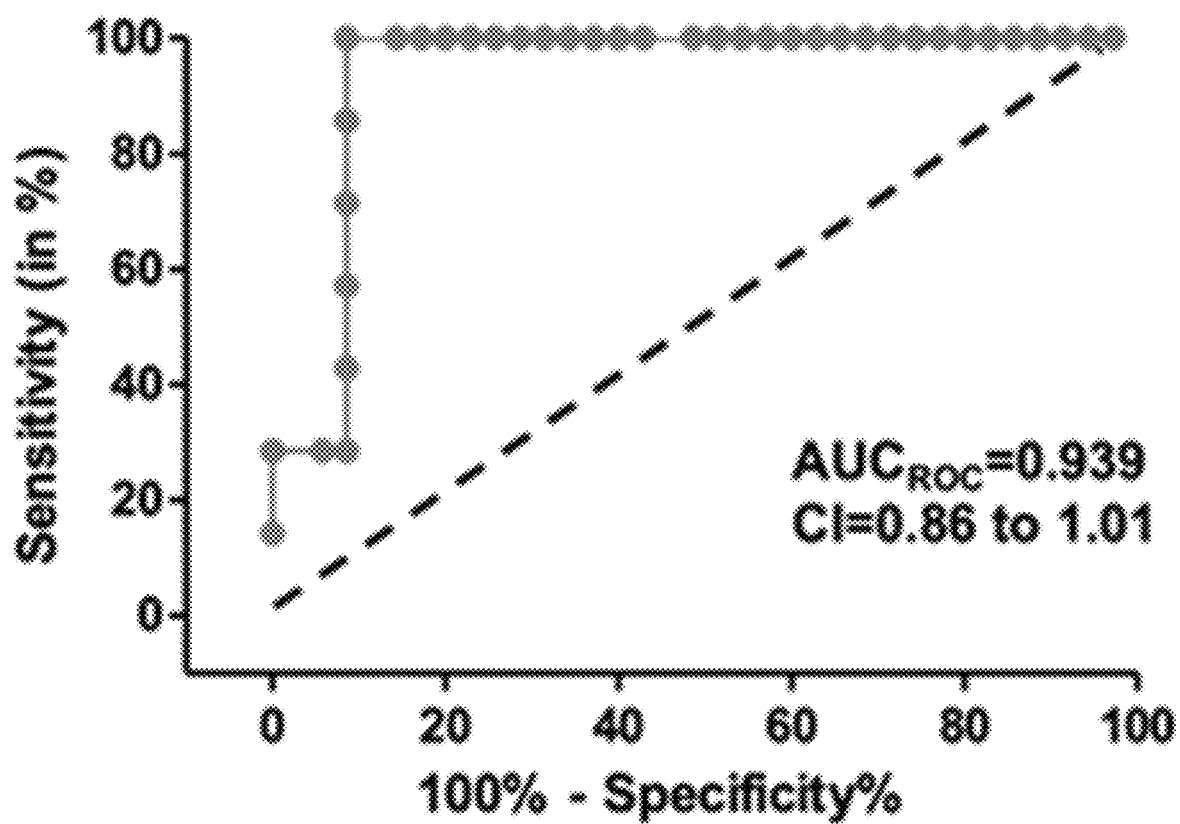

Significant differential response on cell viability toward the chemotherapeutic drugs were identified in between resistant group and sensitive group of the CTC cultures (FIG. 2D, calculated by Mann-Whitney t-test, p=0.0159). With adequate judgement threshold, the CTC cultures from sensitive group showed much lower cell viability than the CTC cultures from the resistant group. The receiver operating characteristic (ROC) curve generated from this window showed high AUC value of 0.939 [confidence interval (CI), 0.86 to 1.01; FIG. 2E]. The data demonstrated that the CTC cultures showed highly relevant drug responses with clinical treatment results, tested by ex vivo drug assay using identical clinical therapeutic drugs. Importantly, the assay requires only $1\sim10^2$ cells for initial seeding, and could generate spheroids for following therapeutic drug screening within 3 weeks.

Example 6

Figure 3A:
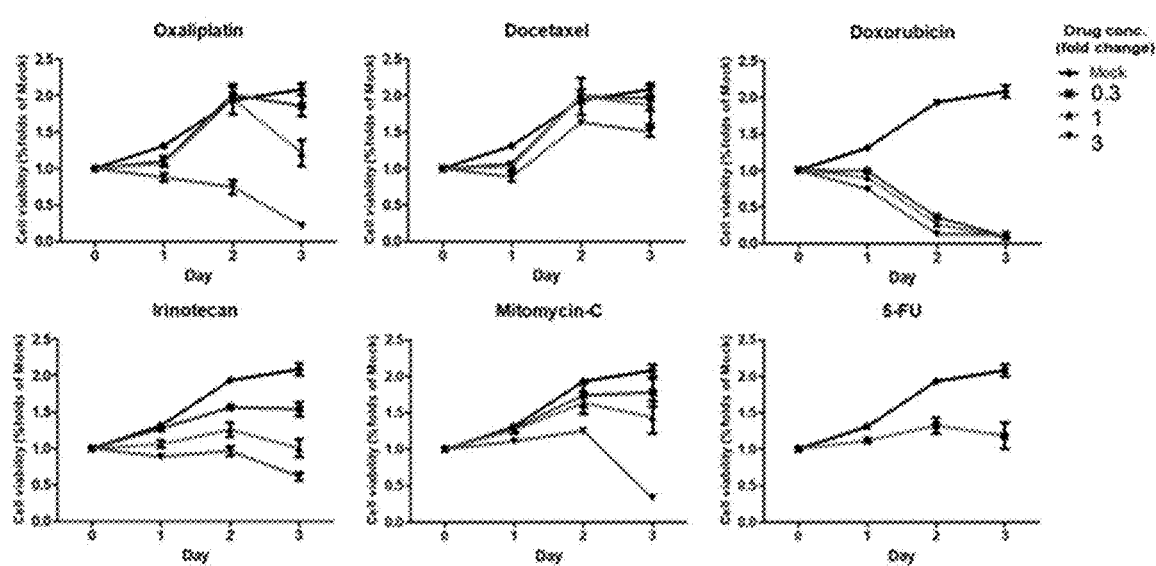
FIGS. 3A-3F show the in vitro drug test results of CTC-derived spheroids and clinical-pathological results of the clinical patient. (A) The drug cytotoxicity assay results on the patient-derived CTC-originated spheroid of patient A. Six chemotherapeutic drugs were tested in this assay include oxaliplatin, docetaxel, doxorubicin, irinotecan, mitomycin-C, and 5-FU. (B and D) The image of the morphology of CTC-derived spheroids after drug panel treatment at day 3. Scale bar=20 µm. (C and E) The normalized viability of CTC-derived spheroids with indicated drug panel after 3 days of treatment. (F) The contrast-enhanced CT images before and after cisplatin/gemcitabine treatment of patient B.
Figure 3B:
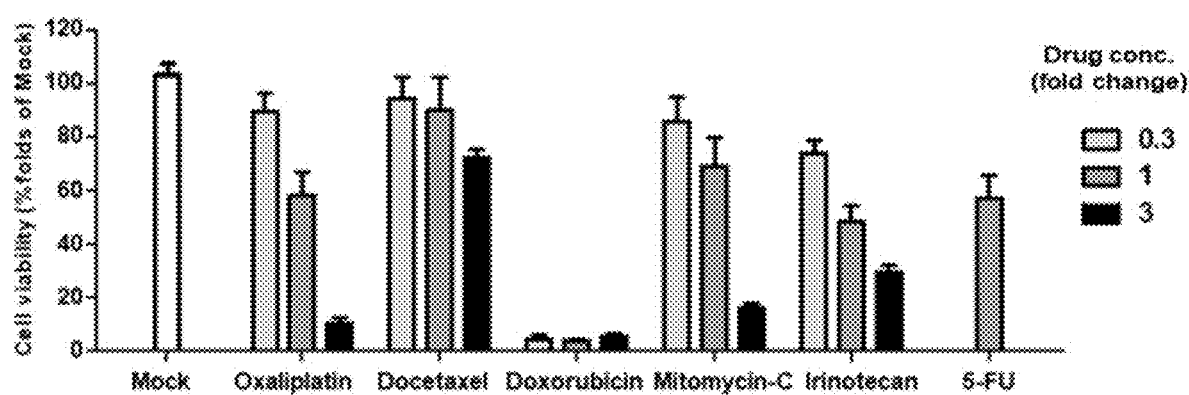
Figure 3C:
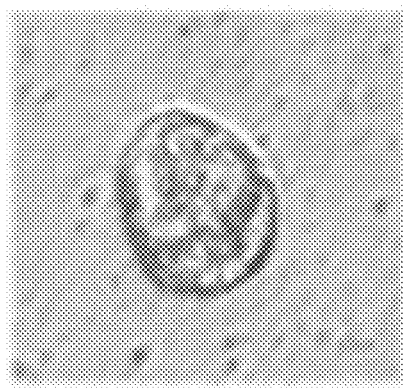
Figure 3C:
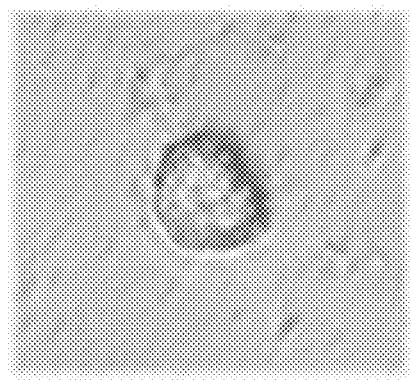
Figure 3C:
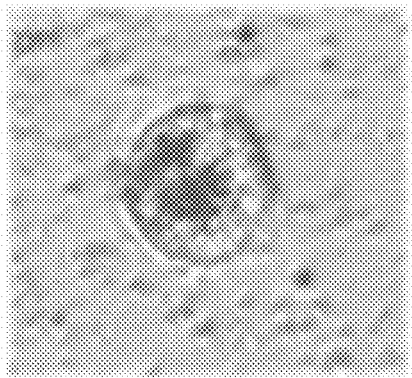
Figure 3C:
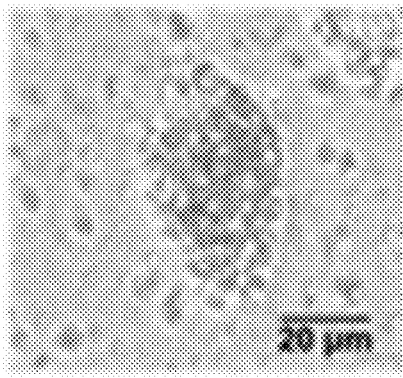
Figure 3D:
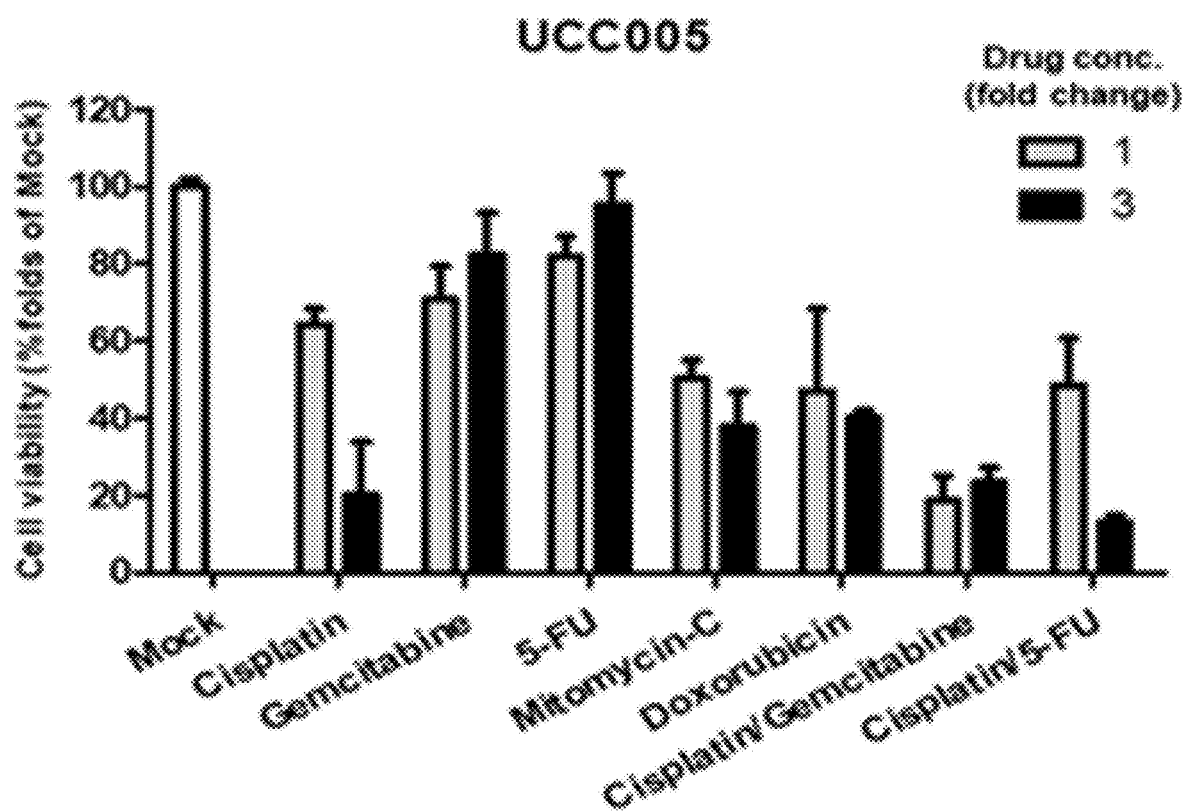
Figure 3E:
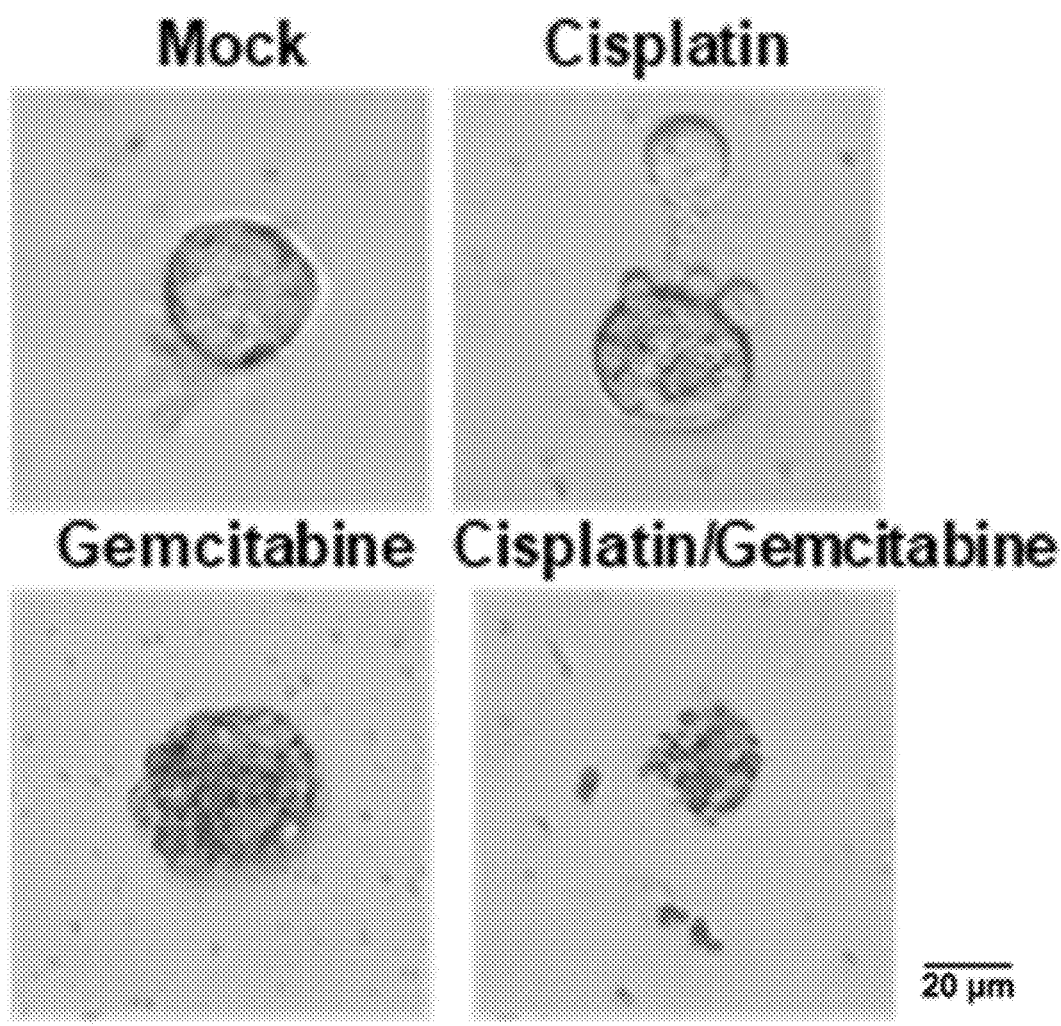
Figure 3F:
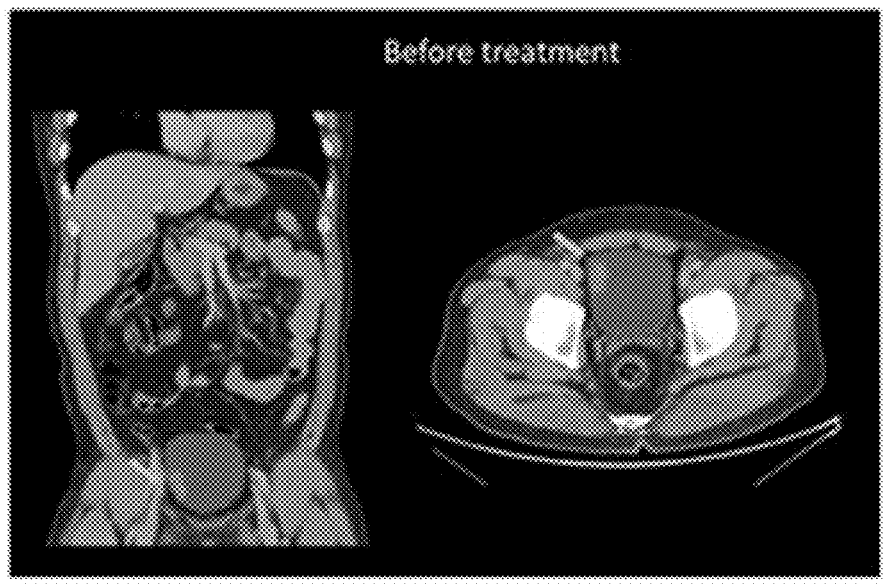
Figure 3F:
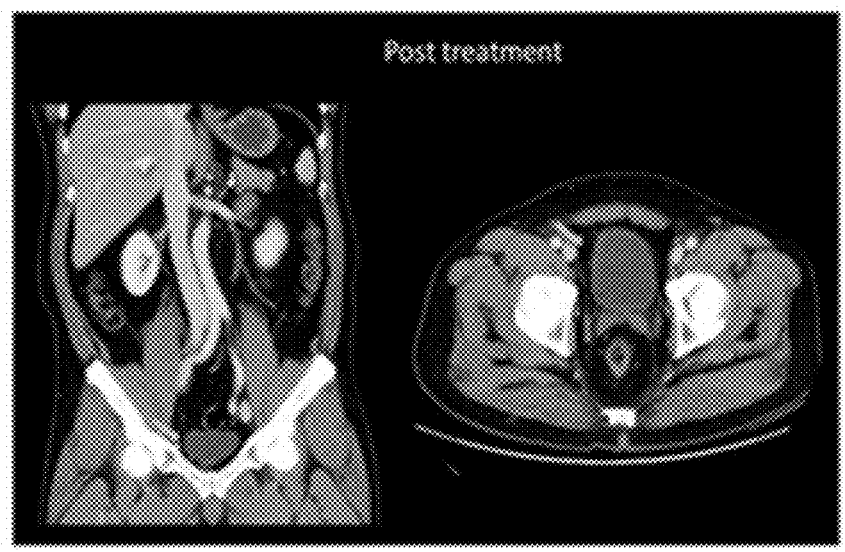
Figure 4A:
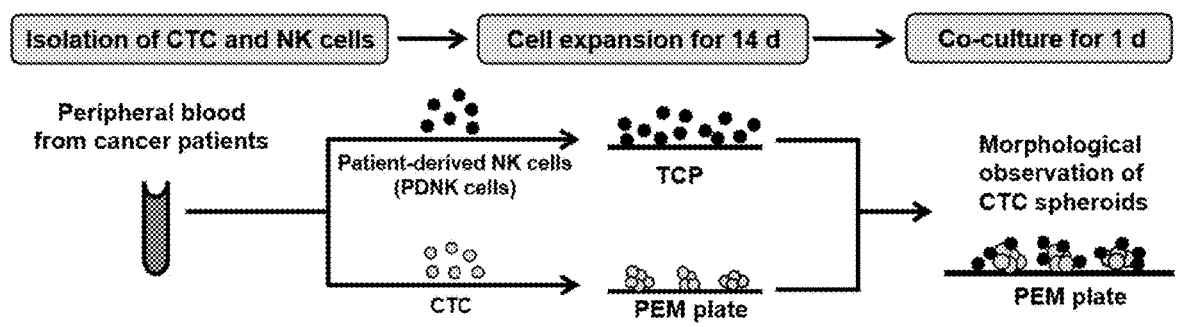
FIG. 4A shows the flow chart illustrating the procedure for determining the efficacy of personalized immune cell therapy on the surface of the present disclosure (denoted as PEM plate).
Figure 4B:
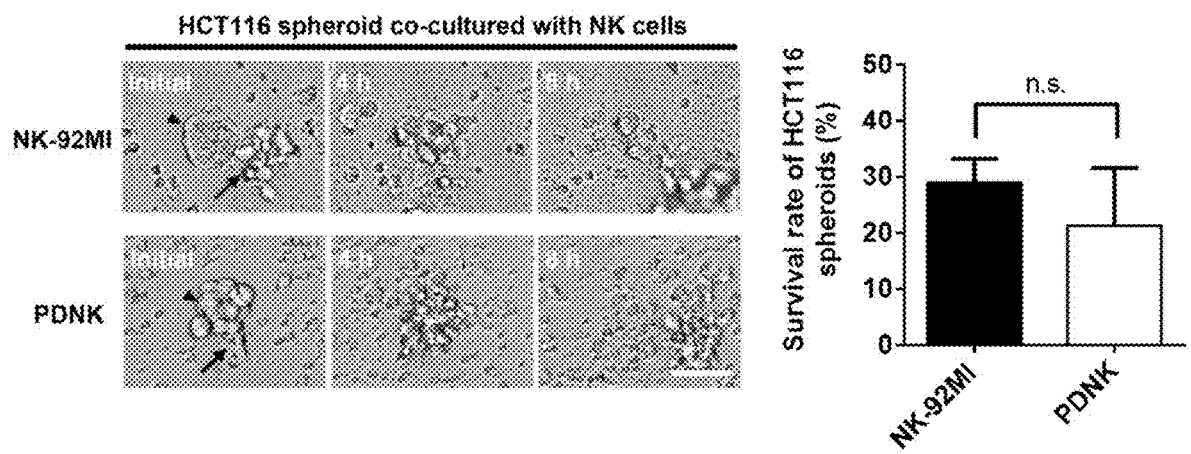
FIG. 4B shows representative time-lapse images indicating the destruction of HCT116 spheroids by NK-92MI and PDNK cells, respectively, on the surface of the present disclosure. Average survival rate of HCT116 spheroids was analyzed after 24 h of co-culture. PDNK cells derived from three individuals was employed, and the number of HCT116 spheroids adopted in each independent experiment was 15-37 for the analysis of survival rate. Arrow head, HCT116 spheroid; Arrow, NK cells. n.s., not significant. Scale bar, 50 mm.
Figure 4C:
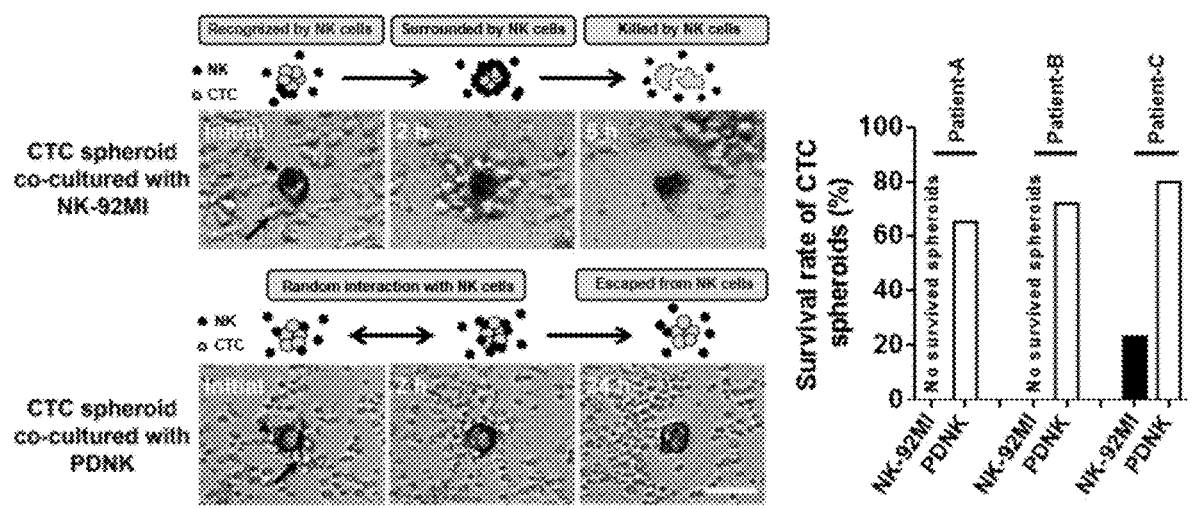
FIG. 4C shows representative time-lapse images demonstrating the different cytotoxicity of autologous PDNK cells and NK-92MI cells against CTC spheroids on RCE platform. Interaction events between CTC spheroids and NK cells were indicated during the co-culture. Survival rate of CTC spheroids derived from three patients was respectively examined after the co-culture with different NK cells for 24 h. 13-58 of CTC spheroids was employed in each independent experiment for the determination of survival rate. Arrow head, CTC spheroid; Arrow, NK cells. Scale bar, 50 mm.

Ex vivo Drug Response Profile of CTC Cultures Correlates with Clinical Treatment Outcome In order to validate the ex vivo drug assay results, we tested single or combination therapeutic agents in CTC cultures derived from blood samples of patients. In patient A, who had been previously treated with oxaliplatin, docetaxel, 5-FU and showed progression disease after clinical treatment. A designed ex vivo drug assay with both used and potential candidate drug panel including oxaliplatin, docetaxel, 5-FU, doxorubicin, mitomycin-c, and irinotecan was accomplished with time-dependent and dose-dependent manner (FIG. 3A). With regard to the cell morphology, the diameter of CTC spheroid derived from blood samples of patient A was about 30~40 µm with an intact spheroid morphology in untreated mock group. After treatments with oxaliplatin and 5-FU for 3 days, the diameter of CTC spheroid was smaller than the mock group and became leakage in appearance. With doxorubicin treatment, obvious broken morphology was shown in the CTC cultures and represent cell debris around the cell (FIG. 3C). On the other hand, the patient A showed high spheroid viability over 50% on 5-FU and docetaxel treatment whereas lower than 4% under doxorubicin treatment. The results highly match with the clinical treatment outcomes in the treatment resistance on the clinical used drugs. Therefore, doxorubicin was the related promising candidate drug among the un-used drugs (mitomycin-c and irinotecan) for next line treatment (FIG. 3B). Additional ex vivo drug test was also performed on patient B with urothelium cancer. Both the size and cell viability of the CTC cultures treated with cisplatin/gemcitabine combination from patient B were both smaller than the spheroids of untreated mock group or single agent treated spheroid (FIGS. 3C and 3D). As in reality, the patient also showed positive clinical response with significant shrinkage on the tumor mass after cisplatin/gemcitabine combination therapy under CT imaging diagnosis (FIG. 3F). In summary, the results of the CTC-based ex vivo drug sensitivity assay showed highly concordance with clinical patient response. These results demonstrate the feasibility of the drug testing platform for clinical utility in predicting the clinical outcome of drug treatment response.

Example 8

Cocultures of Patient-Derived Tumor Spheroids with Autologous NK Cells from Peripheral Blood Peripheral blood can be used as a source of natural killer (NK) cells. Peripheral blood mononuclear cells (PBMCs) contain 10-12% of circulating NK cells. Patient-derived NK (PDNK) cells were isolated from peripheral blood of a colorectal cancer patient, and then expanded ex vivo for two weeks after the isolation.

A tumor spheroid derived from the colorectal cancer patient was generated on the surface of the invention. To examine the cytotoxicity of PDNK cells on the patient-derived tumor spheroids, the tumor spheroid was co-cultured with PDNK cells for 24 h. The patient-derived tumor spheroids remained intact without morphological change after 24 h of incubation, indicating the PDNK cells are not cytotoxic against the patient-derived tumor spheroids. The result indicated that the autologous PDNK cells could approach the patient-derived tumor spheroid on the surface of the invention, however they did not recognize the patient-derived tumor spheroid as a target of killing.

For comparison, NK-92MI cell line was employed as a side-by-side control group of PDNK cells. The patient-derived tumor spheroid was co-cultured with NK-92MI cells. It was observed that the patient-derived tumor spheroid was recognized and then rapidly encircled by NK-92MI cells within 2 h. Subsequently, the patient-derived tumor spheroid was further disrupted by NK-92MI cells, and the debris of the patient-derived tumor spheroid was observed on the surface of the invention. Analysis showed that the cytotoxicity of NK-92MI cells against the patient-derived tumor spheroid was dramatically higher than that of autologous PDNK cells. Analysis was performed by luminescence-based cell-based or biochemical assays based on luminescence or fluorescence.

Methods and Materials

Immunofluorescence staining and Microscopic Imaging. For immunofluorescence staining, the cells were fixed with 4% paraformaldehyde in PBS buffer for 30 min, permeabilized with 0.1% triton X-100 in PBS buffer for another 30 min, and blocked with 5% BSA for 1 h. Subsequently, cells were stained with colon specific marker rabbit anti-human pan-cytokeratin (panCK, Abcam, Cambridge, UK), followed with goat anti-rabbit 647 secondary antibody and DAPI (Invitrogen) for nuclear stain. Both the unstained and immunostained cells were photographed under Nikon Ti Eclipse inverted fluorescence microscope.

Capture and Release of Circulating Tumor Cells (CTCs) from Clinical Patients. The peripheral blood and tissue samples were obtained from breast and colorectal cancer (CRC), head-&-neck squamous cell carcinoma (HNSCC) and urothelial cancer patients from Chang Gung Memorial Hospital (Linkou, Taoyuan), Taipei Veterans General Hospital (Taipei, Taiwan) and National Taiwan University Hospital (Taipei, Taiwan). Tissues from either surgical resection or needle biopsy were preserved in ice cold DMEM medium and transfer immediately after surgical removal. Total 2 mL of whole blood sample were collected by ethylene-diamine-tetra-acetic acid (EDTA) vacutainer tubes (BD Biosciences) from each patient and was used for CTC capture and release on a CTC-capturing platform.

Spheroid formation on the culture platform of the invention. Collect the cell sample that would be used for cultivation on the culture platform of the invention in suspension medium. Add cell suspension medium into each well. The cells could be cultured under 37° C. incubator with humidified 5% $CO_2$ atmosphere. Exchange half of the culture medium once or twice per week. The cultured spheroids (tumoroids) enables sustain in the culture platform of the invention for more than two weeks depends on the cell density and demand of the spheroid size.

Statistical Analysis. All the statistical analyses were accomplished by using GraphPad Prism software (version 6.0c, La Jolla, CA). The student's t-test was performed for the statistical analysis and the p-value was set at 0.05 to investigate statistic significant differences in between two groups. All representative results were shown as mean ±SEM for at least three replicated experiments.

The invention claimed is:
1. A method of preparing cell cultures, comprising:
 (a) providing a cell culture substrate having a surface comprising polyelectrolyte multilayers and an absorbent polymer, wherein the absorbent polymer is in direct contact with a polycation or a polyanion of the polyelectrolyte multilayers;
 (b) seeding a plurality of cancer cells on the surface, wherein the plurality of cancer cells is obtained from a fluid sample of a cancer patient, and wherein the cancer cells comprise circulating tumor cells; and
 (c) culturing the cancer cells under a suitable medium for a time sufficient to produce cell cultures, wherein the cell cultures comprise three-dimensional (3D) cell cultures comprising a plurality of tumor spheroids adhered to the surface.
2. A method of evaluating a therapeutic agent for cancer, the method comprising:
 (a) preparing cell cultures according to the method of claim 1;

(b) optionally incubating the cell cultures with a plurality of immune cells;
(c) contacting the cell cultures with a therapeutic agent;
(d) evaluating an effect of the therapeutic agent on the cell cultures; and
(e) determining the cancer patient as responsive to the therapeutic agent when the therapeutic agent has an anti-cancer effect on the cell cultures comprising the tumor spheroids; or determining the cancer patient as non-responsive to the therapeutic agent when the therapeutic agent does not have an anti-cancer effect on the cell cultures comprising the tumor spheroids.

3. The method of claim 2, wherein the therapeutic agent is selected from the group consisting of one or more chemotherapeutic drugs, an immune checkpoint inhibitor, a nucleic acid drug, a therapeutic cell composition, and a combination thereof.

4. The method of claim 3, wherein the therapeutic agent comprises an immune checkpoint inhibitor, wherein the cell cultures are further incubated with a plurality of immune cells.

5. The method of claim 4, wherein the immune checkpoint inhibitor is selected from the group consisting of PD-1 inhibitor, a PD-L1 inhibitor, and a CLTA-4 inhibitor.

6. The method of claim 5, wherein the immune checkpoint inhibitor is selected from the group consisting of group consisting of nivolumab, pembrolizumab, cemiplimab, atezolizumab, avelumab, durvalumab, and ipilimumab.

7. The method of claim 3, wherein the therapeutic agent comprises a therapeutic cell composition.

8. The method of claim 7, wherein the therapeutic cell composition comprises T cells, natural killer (NK) or dendritic cells.

9. The method of claim 7, wherein the therapeutic cell composition comprises chimeric antigen receptor T (CAR-T) cells or chimeric antigen receptor-natural killer (CAR-NK) cells.

10. The method of claim 3, wherein the therapeutic agent comprises one or more chemotherapeutic drugs.

11. The method of claim 10, wherein the one or more chemotherapeutic drugs are cytotoxic or cytostatic chemotherapeutic drugs.

12. The method of claim 3, wherein the therapeutic agent comprises a nucleic acid drug.

13. The method of claim 2, wherein the cell cultures are in direct contact with an outermost layer of the polyelectrolyte multilayers; wherein the outermost layer is a polycation or a polyanion.

14. The method of claim 13, wherein the polycation is selected from the group consisting of poly(L-lysine) (PLL), poly(L-arginine) (PLA), poly(L-ornithine) (PLO) or poly(L-histidine) (PLH), and a combination thereof; wherein the polyanion is poly(L-glutamic acid) (PLGA) or poly(L-aspartic acid) (PLAA).

15. A method of treating a cancer by immunotherapy, the method comprising:
(a) evaluating a therapeutic agent for the immunotherapy for a cancer patient according to the method of claim 2; and
(b) administering to the cancer patient responsive to the therapeutic agent a therapeutically effective amount of the therapeutic agent for the immunotherapy.

16. The method of claim 15, wherein the therapeutic agent for the immunotherapy is selected from the group consisting of an immune checkpoint inhibitor, a nucleic acid drug, a therapeutic cell composition, and a combination thereof.

17. The method of claim 1, wherein the medium comprises a Rho-associated protein kinase (ROCK) inhibitor, wherein the ROCK inhibitor is of a structural formula having an isoquinoline, 4-amidopyridine, or 4-amidopyrrolopyridine scaffold.

18. The method of claim 1, wherein the absorbent polymer is selected from the group consisting of poly(vinyl alcohol) (PVA), poly(ethylene glycol) (PEG), PEG-acrylate, polyvinylpyrrolidone (PVP), polyethyleneimine (PEI), poly-L-lactide (PLLA), poly-D-lactide (PDLA), poly(L-lactide-co-D,L-lactide) (PLDLLA), poly(glycolic acid) (PGA), poly(lactic-co-glycolic acid) (PL-co-GA), poly(methyl methacrylate) (PMMA), poly(hydroxyethyl methacrylate) (p-HEMA), and derivatives thereof.

19. The method of claim 1, wherein the polyelectrolyte multilayers comprise n bilayers of polycation and polyanion; wherein n is an integer number ranging from 1 to 30.

20. A method of preparing cell cultures, comprising:
(a) providing a cell culture substrate having a surface comprising polyelectrolyte multilayers and an absorbent polymer, wherein the absorbent polymer is in direct contact with a polycation or a polyanion of the polyelectrolyte multilayers;
(b) seeding a plurality of cancer cells on the surface, wherein the plurality of cancer cells is obtained from a fluid sample of a cancer patient; and
(c) culturing the cancer cells under a suitable medium for a time sufficient to produce cell cultures, wherein the cell cultures comprise three-dimensional (3D) cell cultures comprising a plurality of tumor spheroids adhered to the surface, and wherein the medium comprises a Rho-associated protein kinase (ROCK) inhibitor, wherein the ROCK inhibitor is of a structural formula having an isoquinoline, 4-amidopyridine, or 4-amidopyrrolopyridine scaffold.

21. The method of claim 20, wherein the cancer cells comprise circulating tumor cells.

22. A method of evaluating a therapeutic agent for cancer, the method comprising:
(a) preparing cell cultures by:
(i) providing a cell culture substrate having a surface comprising polyelectrolyte multilayers and an absorbent polymer, wherein the absorbent polymer is in direct contact with a polycation or a polyanion of the polyelectrolyte multilayers;
(ii) seeding a plurality of cancer cells on the surface, wherein the plurality of cancer cells is obtained from a fluid sample of a cancer patient, wherein the cell cultures are in direct contact with an outermost layer of the polyelectrolyte multilayers, and wherein the outermost layer is a polycation or a polyanion; and
(iii) culturing the cancer cells under a suitable medium for a time sufficient to produce cell cultures, wherein the cell cultures comprise three-dimensional (3D) cell cultures comprising a plurality of tumor spheroids adhered to the surface;
(b) optionally incubating the cell cultures with a plurality of immune cells;
(c) contacting the cell cultures with a therapeutic agent;
(d) evaluating an effect of the therapeutic agent on the cell cultures; and
(e) determining the cancer patient as responsive to the therapeutic agent when the therapeutic agent has an anti-cancer effect on the cell cultures comprising the tumor spheroids; or determining the cancer patient as non-responsive to the therapeutic agent when the therapeutic agent does not have an anti-cancer effect on the cell cultures comprising the tumor spheroids.

* * * * *